(12) United States Patent
Robinson

(10) Patent No.: US 11,590,000 B2
(45) Date of Patent: Feb. 28, 2023

(54) EXPANDABLE, ADJUSTABLE INTER-BODY FUSION DEVICES AND METHODS

(71) Applicant: SPECTRUM SPINE IP HOLDINGS, LLC, Atlanta, GA (US)

(72) Inventor: James C. Robinson, Atlanta, GA (US)

(73) Assignee: Spectrum Spine IP Holdings, LLC, Atlanta, GA (US)

( * ) Notice: Subject to any disclaimer, the term of this patent is extended or adjusted under 35 U.S.C. 154(b) by 670 days.

(21) Appl. No.: 16/708,209

(22) Filed: Dec. 9, 2019

(65) Prior Publication Data

US 2020/0113706 A1    Apr. 16, 2020

Related U.S. Application Data

(63) Continuation of application No. 16/210,240, filed on Dec. 5, 2018, now Pat. No. 10,500,064, which is a continuation of application No. 15/521,995, filed as application No. PCT/US2015/057892 on Oct. 28, 2015, now Pat. No. 10,285,824.

(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4425* (2013.01); *A61F 2/4455* (2013.01); *A61F 2/4611* (2013.01); *A61F 2002/304* (2013.01); *A61F 2002/3054* (2013.01); *A61F 2002/30261* (2013.01); *A61F 2002/30405* (2013.01); *A61F 2002/30507* (2013.01); *A61F 2002/30538* (2013.01); *A61F 2002/30556* (2013.01); *A61F 2002/30579* (2013.01); *A61F 2002/30593* (2013.01); *A61F 2002/30622* (2013.01);
(Continued)

(58) Field of Classification Search
CPC ..... A61F 2002/443; A61F 2/44; A61F 2/4455
See application file for complete search history.

(56) References Cited

U.S. PATENT DOCUMENTS 5,800,550 A * 9/1998 Sertich .................. A61F 2/4611
                                                      606/247
6,039,761 A   3/2000 Li et al.
(Continued)

FOREIGN PATENT DOCUMENTS

WO    2013158294 A1    10/2013
WO    2016069796 A1    5/2016

OTHER PUBLICATIONS

Interventional Spine, Opticage (R) information.

*Primary Examiner* — David W Bates
(74) *Attorney, Agent, or Firm* — David L. King

(57) ABSTRACT

An expandable, adjustable inter-body fusion device is presented. The inter-body fusion device can have a first plate, a second plate, and an insert positioned substantially there between the first plate and the second plate. The first plate, the second plate, and the insert define an interior cavity. Moving the insert longitudinally with respect to the first and second plates increases or decreases the distance of the first plate with respect to the second plate, effectively expanding the inter-body fusion device and increasing the volume of the interior cavity. The angle between the first plate and the second plate is selectively adjustable.

9 Claims, 28 Drawing Sheets

Related U.S. Application Data

(60) Provisional application No. 62/069,362, filed on Oct. 28, 2014.

(52) U.S. Cl.
CPC ............... *A61F 2002/30904* (2013.01); *A61F 2002/4628* (2013.01)

(56) References Cited

U.S. PATENT DOCUMENTS

| | | | |
|---|---|---|---|
| 6,176,882 B1 | 1/2001 | Biedermann et al. | |
| 6,641,614 B1 * | 11/2003 | Wagner | A61F 2/4455 623/17.15 |
| 7,217,291 B2 * | 5/2007 | Zucherman | A61F 2/4425 623/17.13 |
| D566,276 S | 4/2008 | Blain | |
| 8,062,375 B2 | 11/2011 | Glerum et al. | |
| 8,105,382 B2 | 1/2012 | Olmos et al. | |
| 8,216,316 B2 | 7/2012 | Kirschman | |
| 8,343,224 B2 | 1/2013 | Lynn et al. | |
| 8,366,777 B2 | 2/2013 | Matthis et al. | |
| 8,382,842 B2 | 2/2013 | Greenhalgh et al. | |
| 8,398,713 B2 | 3/2013 | Weiman | |
| 8,568,481 B2 | 10/2013 | Olmos et al. | |
| 8,845,728 B1 | 9/2014 | Abdou | |
| 8,852,243 B2 | 10/2014 | Morgenstern et al. | |
| 8,852,279 B2 | 10/2014 | Weiman | |
| 8,940,049 B1 | 1/2015 | Jimenez et al. | |
| 9,358,123 B2 | 6/2016 | McLuen et al. | |
| 9,486,328 B2 | 11/2016 | Jimenez et al. | |
| 9,492,288 B2 | 11/2016 | Wagner et al. | |
| 9,522,070 B2 | 12/2016 | Flower et al. | |
| 9,532,883 B2 | 1/2017 | McLuen et al. | |
| 9,668,876 B2 | 6/2017 | Blain et al. | |
| 9,839,527 B2 | 12/2017 | Robinson | |
| 9,839,528 B2 | 12/2017 | Weiman et al. | |
| 9,937,053 B2 | 4/2018 | Melkent et al. | |
| 9,987,143 B2 | 6/2018 | Robinson | |
| 10,098,757 B2 | 10/2018 | Logan et al. | |
| 10,111,760 B2 | 10/2018 | Knapp et al. | |
| 10,154,911 B2 * | 12/2018 | Predick | A61B 17/8858 |
| 10,159,583 B2 | 12/2018 | Dietzel et al. | |
| 10,219,914 B2 | 3/2019 | Faulhaber | |
| 2004/0172134 A1 | 9/2004 | Berry | |
| 2006/0253201 A1 | 11/2006 | McLuen | |
| 2007/0270968 A1 | 11/2007 | Baynham et al. | |
| 2009/0222100 A1 | 9/2009 | Cipoletti et al. | |
| 2010/0204795 A1 | 8/2010 | Greenhalgh | |
| 2010/0249933 A1 | 9/2010 | Trieu | |
| 2010/0292796 A1 | 11/2010 | Greenhalgh et al. | |
| 2011/0282453 A1 | 11/2011 | Greenhalgh et al. | |
| 2012/0121774 A1 | 5/2012 | Marjeram et al. | |
| 2013/0211526 A1 | 8/2013 | Alheidt et al. | |
| 2014/0121774 A1 | 5/2014 | Glerum et al. | |
| 2014/0296984 A1 | 10/2014 | Etminan | |
| 2016/0166396 A1 | 6/2016 | McClintock | |
| 2017/0042695 A1 | 2/2017 | Foley et al. | |
| 2017/0105844 A1 | 4/2017 | Kuyler et al. | |
| 2017/0333198 A1 | 11/2017 | Robinson | |
| 2018/0318101 A1 | 11/2018 | Engstrom | |

* cited by examiner

EXPANDABLE, ADJUSTABLE INTER-BODY FUSION DEVICES AND METHODS

CROSS-REFERENCE TO RELATED APPLICATIONS

This application is a continuation of application Ser. No. 16/210,240, filed on Dec. 5, 2018, now U.S. Pat. No. 10,500,064, which is a continuation of application Ser. No. 15/521,995, filed on Apr. 26, 2017, now U.S. Pat. No. 10,285,824 filed as application No. PCT/US2015/057892 filed on Oct. 28, 2015 that claims the benefit of and priority to U.S. Provisional Patent 62/069,362, filed Oct. 28, 2014, which is incorporated in its entirety in this document by reference.

FIELD OF THE INVENTION

This invention relates generally to spinal surgery, and more particularly to devices and methods for stabilization of the spine in association with placement of an expandable inter-body construct with an adjustable construct angle for inter-body fusion or the like.

BACKGROUND OF THE INVENTION

Damage or disease that affects the spinal disc within an individual's spinal column may lead to neurologic impairment with possible permanent damage to the surrounding tissue. Maintaining proper anatomic spacing and lordosis within the spine is critical to ensuring continued functionality of the surrounding tissue and for the spinal column, the spinal cord and nerve roots and therefore, avoidance of long term serious neurological impairment.

Typically, spinal implants that are used as a spacer type of device have a fixed overall length and are implanted without the ability to adjust the degree of expansion or curvature without using multiple insertion instrumentation. Some of the known procedures for introducing spinal implants comprise Anterior Lumbar Inter-body Fusion ("ALIF"), Lateral Lumbar Inter-body Fusion ("LLIF"), Posterior Lumbar Inter-body Fusion ("PLIF"), Oblique Lumbar Inter-body Fusion ("OLIF"), Direct Lateral Fusion ("DLIF"), Transforaminal Lumbar Interbody Fusion ("TLIF"), and the like. A need remains for an expandable, adjustable spacer type of implant that allows the surgeon to insert the implant in an unexpanded position to minimize the size of the surgical incision, facilitate the operative technique and decrease patient morbidity.

SUMMARY

Presented herein is an inter-body fusion device, or implant, for use in spinal surgery. In one aspect, the inter-body fusion device can be an expandable fusion device having an expandable height and volume. In another aspect, the inter-body fusion device can be an adjustable fusion device such that an angle formed between an upper hone contact surface and a lower bone contact surface is selectively adjustable by the surgeon.

In one aspect, the inter-body fusion device comprises a first plate, a second plate, and an insert positioned substantially therebetween the first plate and the second plate. The first plate, the second plate, and the insert define an interior cavity. In one aspect, moving at least a portion of the insert longitudinally with respect to the first and second plates in a first direction increases the distance between the first plate relative to the second plate, effectively expanding the inter-body fusion device and increasing the volume of the interior cavity. In another aspect, moving at least a portion of the insert longitudinally with respect to the first and second plates in the first direction increases the angle formed between the first plate relative to the second plate.

It is contemplated that this technology can be used for a variety of implants used for a variety of spinal procedures. These procedures include, but are not limited to OLIF (anterior or posterior), DLIF, PLIF, TLIF, ALIF, and LLIF. So, depending upon the procedure and point of insertion for the implant, the geometry of the implant can differ.

In an exemplified aspect, at least one of the first plate and the second plate define at least one graft window that is in communication with the interior cavity.

Also presented herein is a method of using an inter-body fusion device during an inter-body fusion procedure. In one aspect, the method comprises accessing the desired disc space, choosing the correct insert size with the appropriate height range, inserting the inter-body fusion device into the desired area in the disc space, expanding the inter-body fusion device from a first unexpanded position to a second expanded position and adjusting the angle formed between the first plate relative to the second plate to a desired angle. An additional step of packing the interior cavity via with bone fusion material either prior to or after expansion is also contemplated.

Related methods of operation are also provided. Other apparatuses, methods, systems, features, and advantages of the inter-body fusion device and the method of its use will be or become apparent to one with skill in the art upon examination of the following figures and detailed description. It is intended that all such additional apparatuses, methods, systems, features, and advantages be included within this description, be within the scope of the inter-body fusion device and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DESCRIPTION OF THE INVENTION

Figure 1:
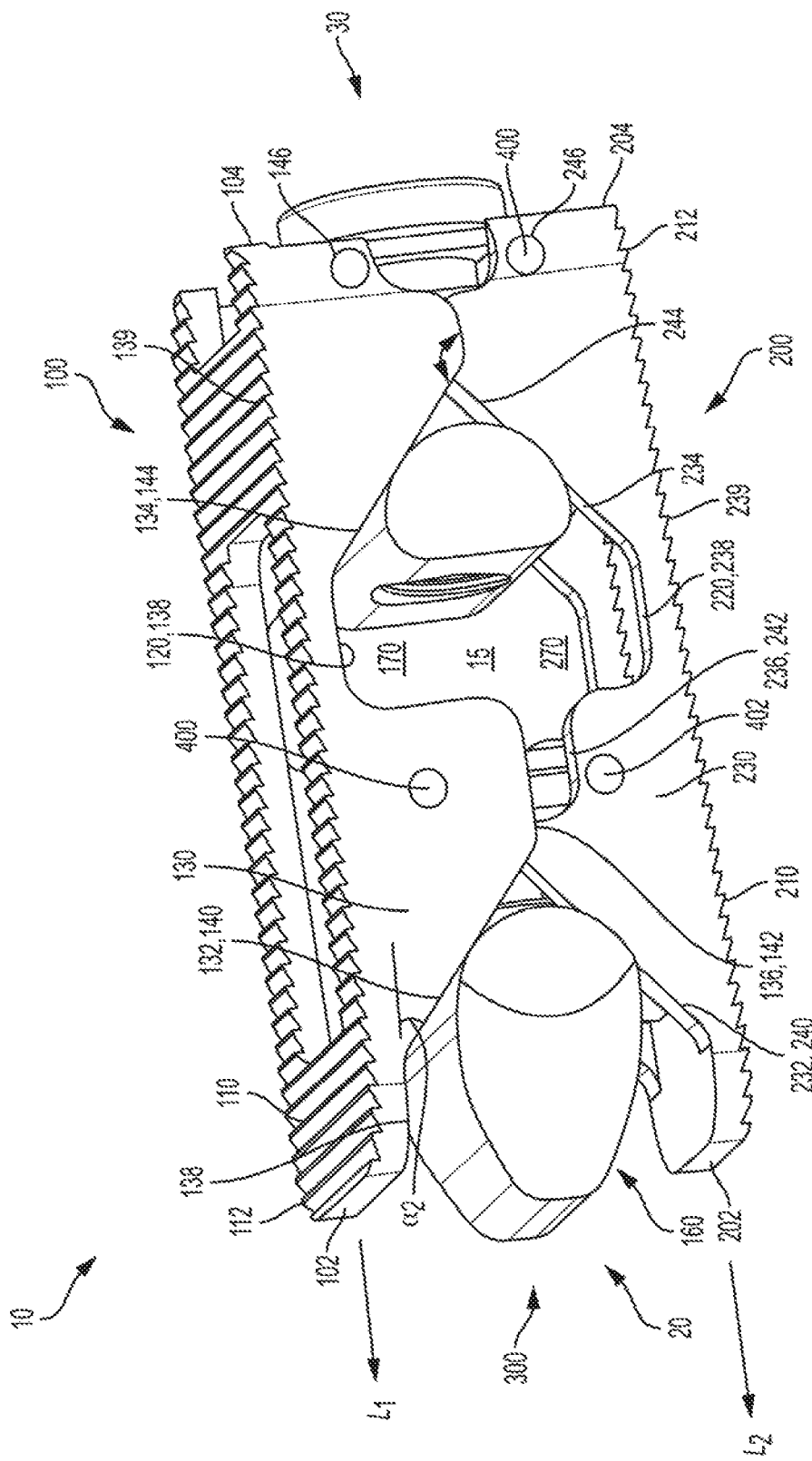
FIG. 1 is a front perspective view of one embodiment of an expandable, adjustable inter-body fusion device in a second expanded position, the device comprising a first plate, a second plate and an insert, according to one aspect.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

In one aspect, presented herein is an inter-body fusion device for use in spinal surgery, such as, but not limited to, ALIF, OLIF, TLIF, LLIF, PLIF, and DLIF procedures. In another aspect, the inter-body fusion device can be an expandable inter-body fusion device such that a height of the device can be selectively adjusted by a user, such as a surgeon. In a further aspect, the inter-body fusion device can be an adjustable fusion device such that a device angle formed between an upper bone contact surface and a lower bone contact surface is selectively adjustable by the user. In another aspect, the inter-body fusion device can be an expandable, adjustable inter-body fusion device having a selectively expandable height and a selectively adjustable device angle.

In one aspect and as illustrated in FIGS. 1-4, the inter-body fusion device 10 comprises a first plate 100, a second plate 200, and an insert 300 positioned substantially therebetween the first plate 100 and the second plate 200. The first plate has a leading edge 102, a trailing edge 104, an upper bone contact surface 110 and an opposed first plate inner surface 120. The second plate 200 has a leading edge 202, a trailing edge 204, a lower bone contact surface 210 and an opposed second plate inner surface 220. In one aspect, the first plate 100, the second plate 200, and the insert 300 define an interior cavity 15.

The inter-body fusion device 10 has a leading end 20 and a trailing end 30. In one aspect, moving the insert 300 longitudinally with respect to the first plate 100 and the second plate 200 (that is, either toward the leading end 20 or toward the trailing end 30 of the device) can increase the distance between the first plate relative to the second plate, effectively expanding the inter-body fusion device and increasing the volume of the interior cavity 15. In another aspect, a device angle $\alpha_1$ formed between a longitudinal axis $L_1$ of the first plate 100 and a longitudinal axis $L_2$ of the second plate 200 can be selectively adjusted by a user to vary the volume of the interior cavity and/or better position the device 10 in the disc space. For example, the device angle $\alpha_1$ can be substantially 0 degrees such that the first plate and the second plate are substantially parallel to each other. In other examples, the device angle $\alpha_1$ can be an acute angle of about 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 20 degrees, 25 degrees, 30 degrees, 35 degrees, 40 degrees, 45 degrees or greater than about 45 degrees.

At least one of the first plate 100 and the second plate 200 has at least one longitudinal sidewall 130, 230 extending substantially between the respective inner surface 120, 220 and bone contact surface 110, 210. In one aspect, the at least one longitudinal sidewall 130, 230 comprises a plurality of longitudinal sidewalls. For example, the longitudinal sidewall can comprise two longitudinal sidewalls. In another aspect, the longitudinal sidewall(s) can be positioned substantially near a peripheral edge 139, 239 of the first and/or second plate.

In one aspect, the longitudinal sidewall 130 of the first plate 100 can comprise at least one ramp 132 having an inclined surface 134. That is, at least a portion of the inner surface 120 of the first plate can be an inclined surface that is at an acute surface angle $\alpha_2$ relative to the longitudinal axis $L_1$ of the first plate. For example, the surface angle $\alpha_2$ can be about 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 20 degrees, 25 degrees, 30 degrees, 35 degrees, 40 degrees, 45 degrees or greater than about 45 degrees. In another aspect, the longitudinal sidewall of the first plate 100 can further comprise at least one substantially flat surface 136 that is substantially parallel to the longitudinal axis $L_1$ of the first plate. Optionally, the longitudinal sidewall 130 of the first plate 100 can comprise an upper flat surface 138, a first inclined surface 140, a lower flat surface 142 and a second inclined surface 144. In this aspect, the upper flat surface and the lower flat surface can be spaced from each other a predetermined distance that is less than the height of the insert 300. Alternatively, the upper flat surface 138 and the lower flat surface 142 can be spaced from each other a predetermined distance that is greater than or equal to the height of the insert. In another aspect, the first inclined surface 140 and the second inclined surface 144 can be at the same surface angle $\alpha_2$ relative to the longitudinal axis $L_1$ of the first plate 100. Optionally, however, the first inclined surface and the second inclined surface can be at a different surface angle $\alpha_2$ relative to the longitudinal axis $L_1$ of the first plate. At least one pin bore 146 can be defined in a portion of the longitudinal sidewall 130.

In one aspect, the longitudinal sidewall 230 of the second plate 200 can comprise at least one ramp 232 having an inclined surface 234. That is, at least a portion of the second plate inner surface 220 can be an inclined surface that is at an acute surface angle $\alpha_3$ relative to the longitudinal axis $L_2$ of the second plate. For example, the surface angle $\alpha_3$ can be about 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 20 degrees, 25 degrees, 30 degrees, 35 degrees, 40 degrees, 45 degrees or greater than about 45 degrees. In another aspect, the longitudinal sidewall of the second plate 200 can further comprise at least one substantially flat surface 236 that is substantially parallel to the longitudinal axis $L_2$ of the second plate. Optionally, the longitudinal sidewall 230 of the second plate 200 can comprise a lower flat surface 238, a first inclined surface 240, an upper flat surface 242 and a second inclined surface 244. In this aspect, the upper flat surface and the lower flat surface can be spaced from each other a predetermined distance that is less than the height of the insert 300. Alternatively, the upper flat surface 242 and the lower flat surface 238 can be spaced from each other a predetermined distance that is greater than or equal to the height of the insert. In another aspect, the first inclined surface 240 and the second inclined surface 244 can be at the same surface angle $\alpha_3$ relative to the longitudinal axis $L_2$ of the second plate 200. Optionally, however, the first inclined surface and the second inclined surface can be at a different surface angle $\alpha_3$ relative to the longitudinal axis $L_2$ of the second plate. At least one pin bore 246 can be defined in a portion of the longitudinal sidewall 230.

Figure 5:
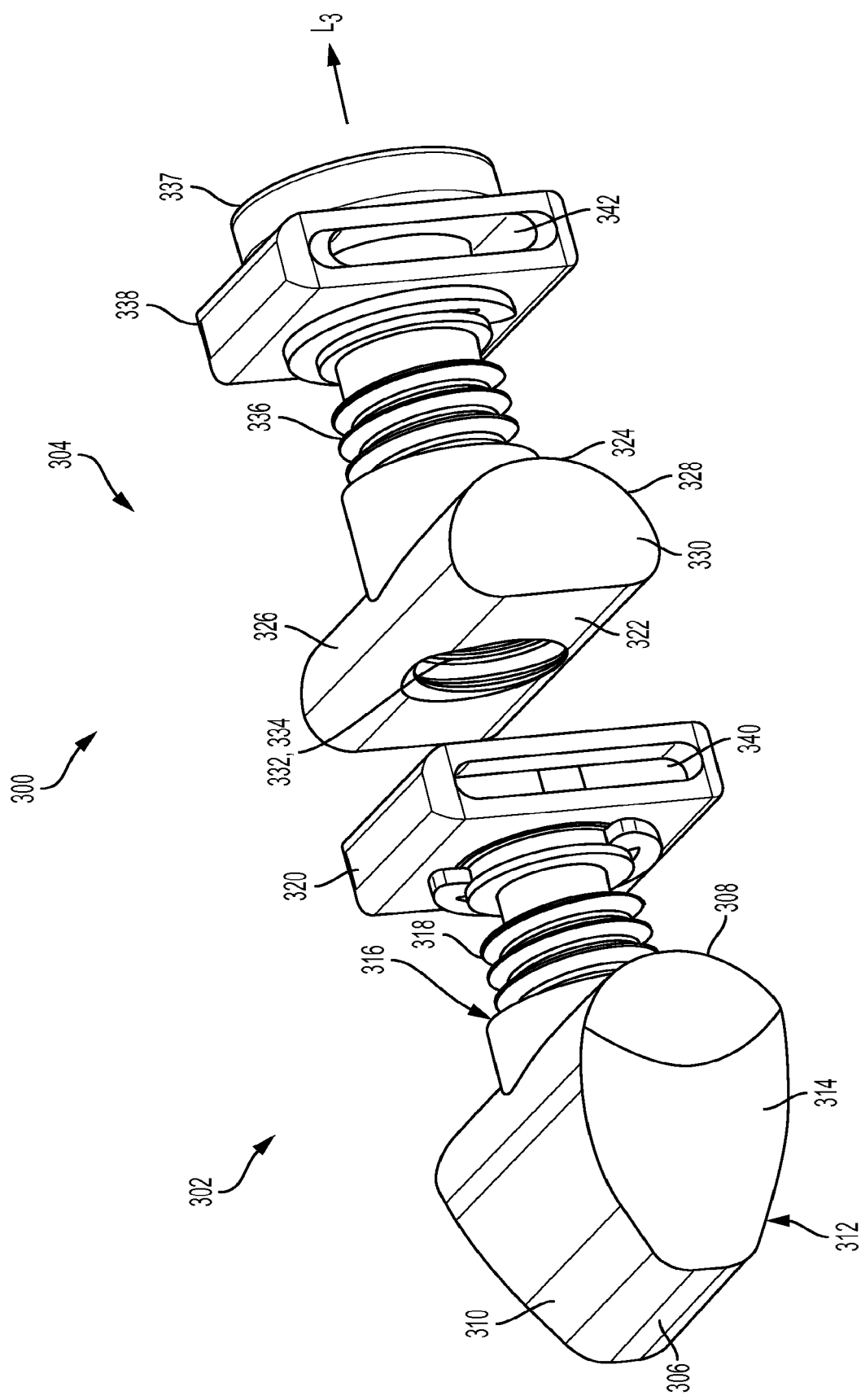
FIG. 5 is front perspective view of the insert of FIG. 1, according to one aspect.
Figure 6:
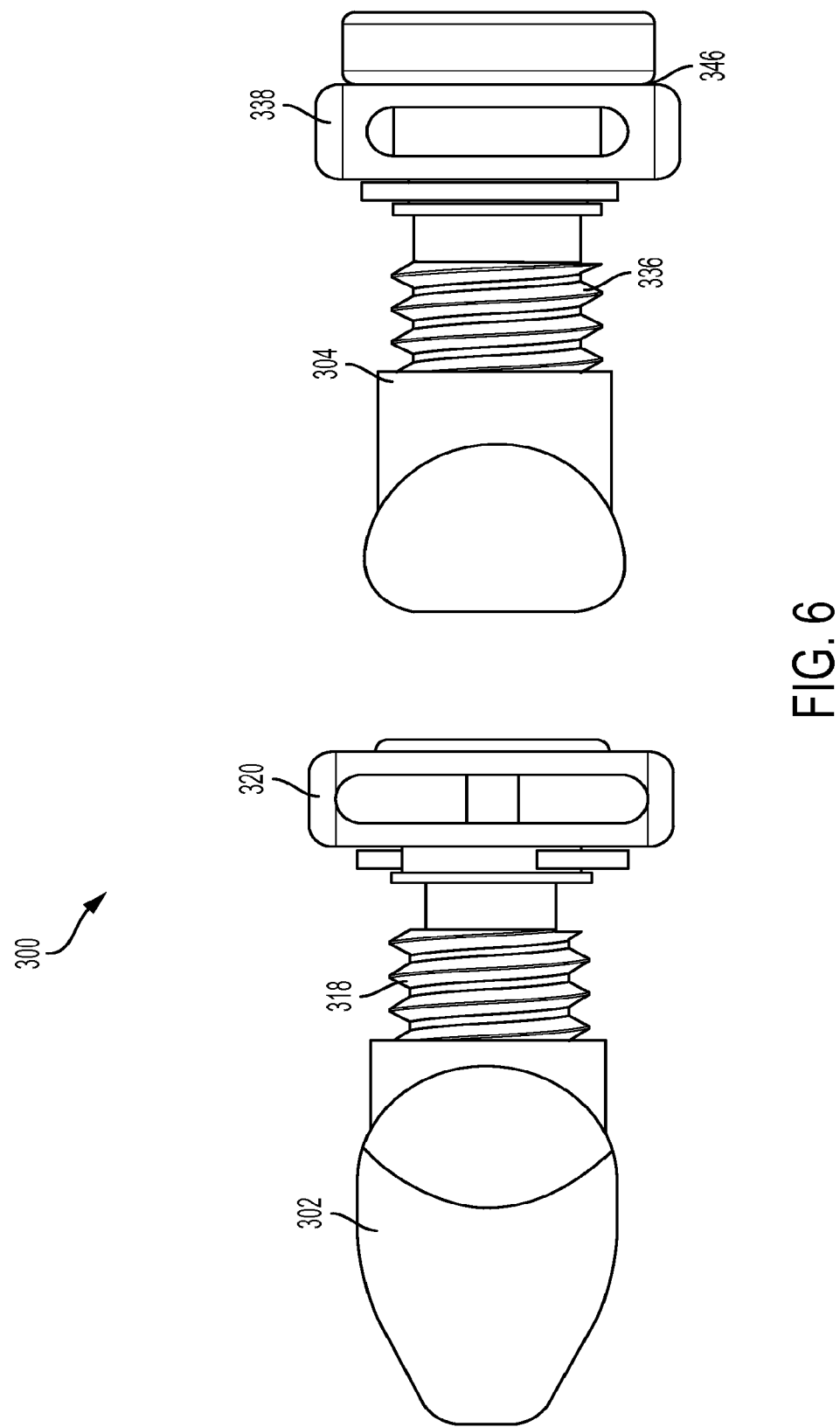
FIG. 6 is a side elevational view of the insert of FIG. 5.
Figure 7:
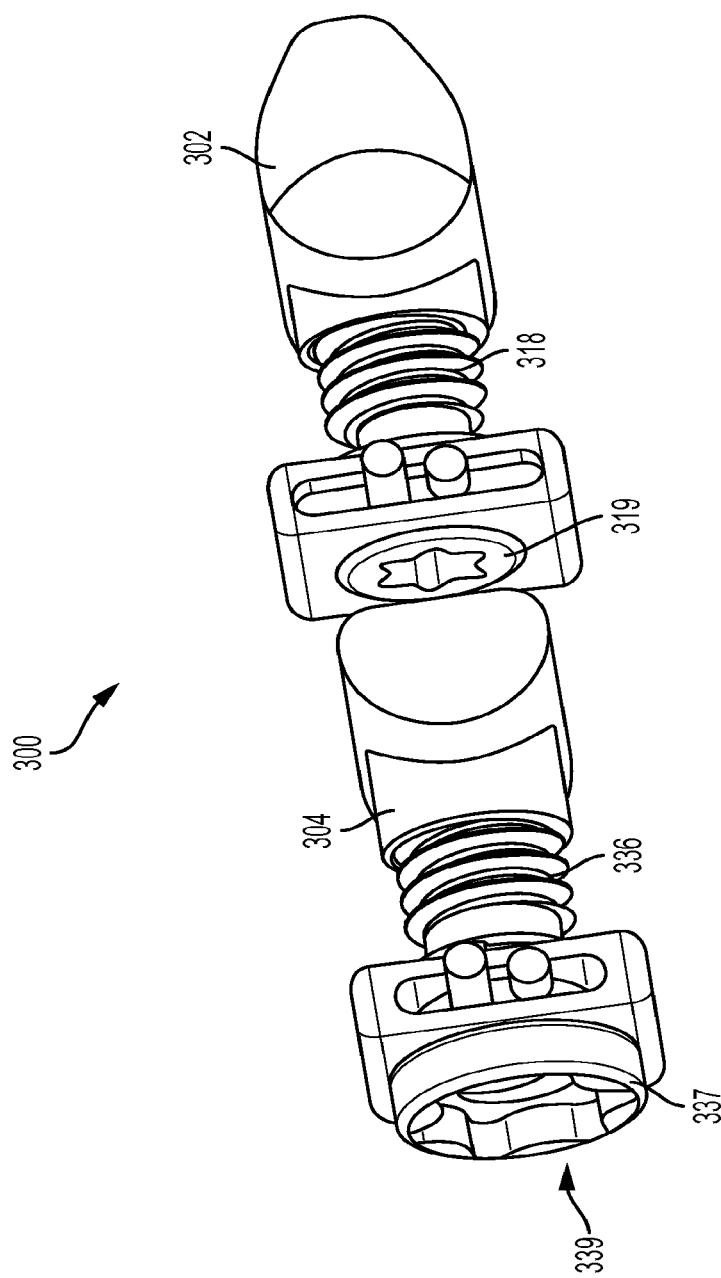
FIG. 7 is a rear perspective view of the insert of FIG. 5.
Figure 8:
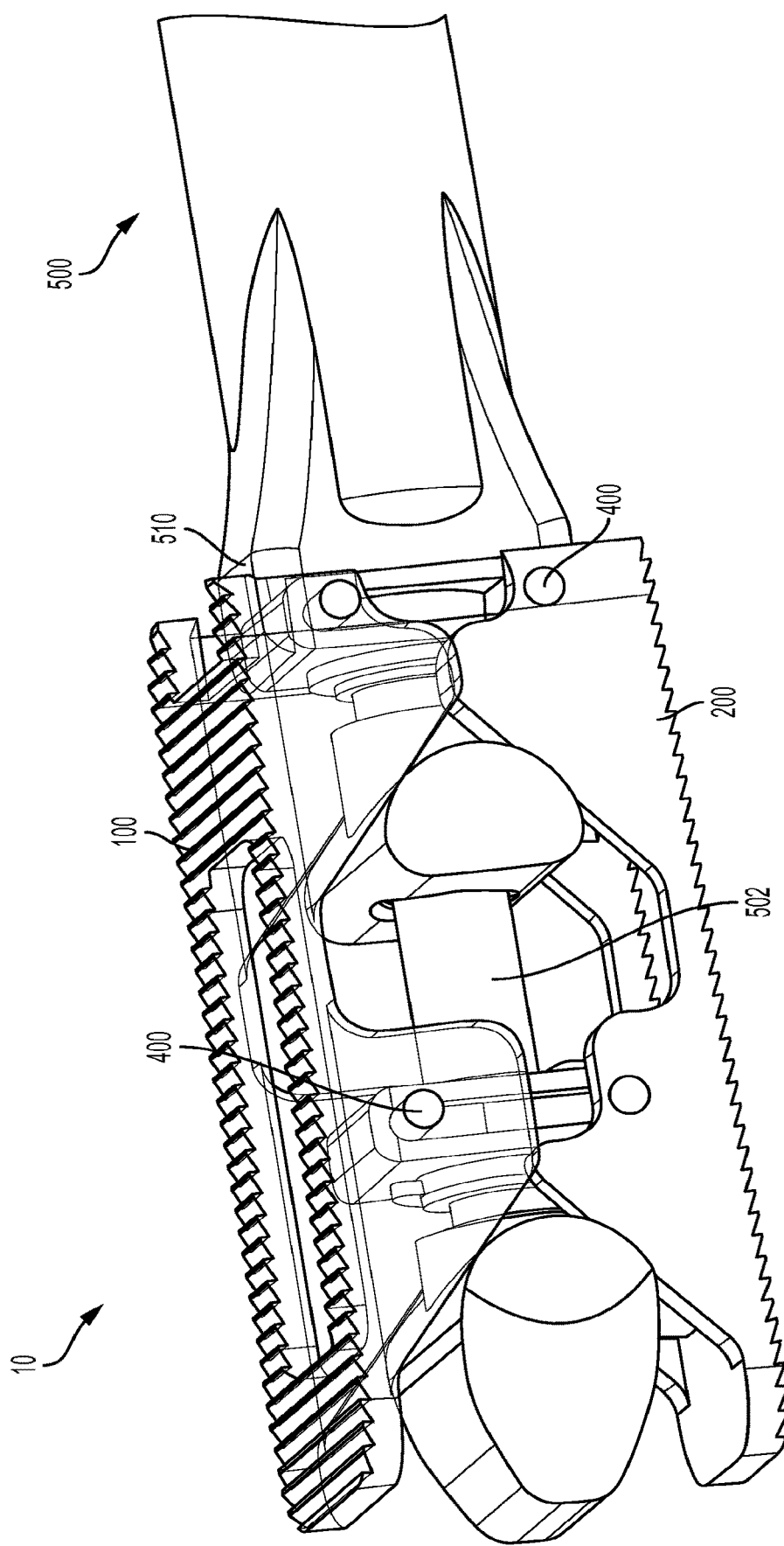
FIG. 8 is a front perspective of the inter-body fusion device of FIG. 1 in the second expanded position, in which the device angle between the first plate and the second plate is substantially 0 degrees, and in which the first plate is illustrated transparently for clarity, showing the inter-body fusion device coupled to a device driver, according to one aspect.
Figure 9:
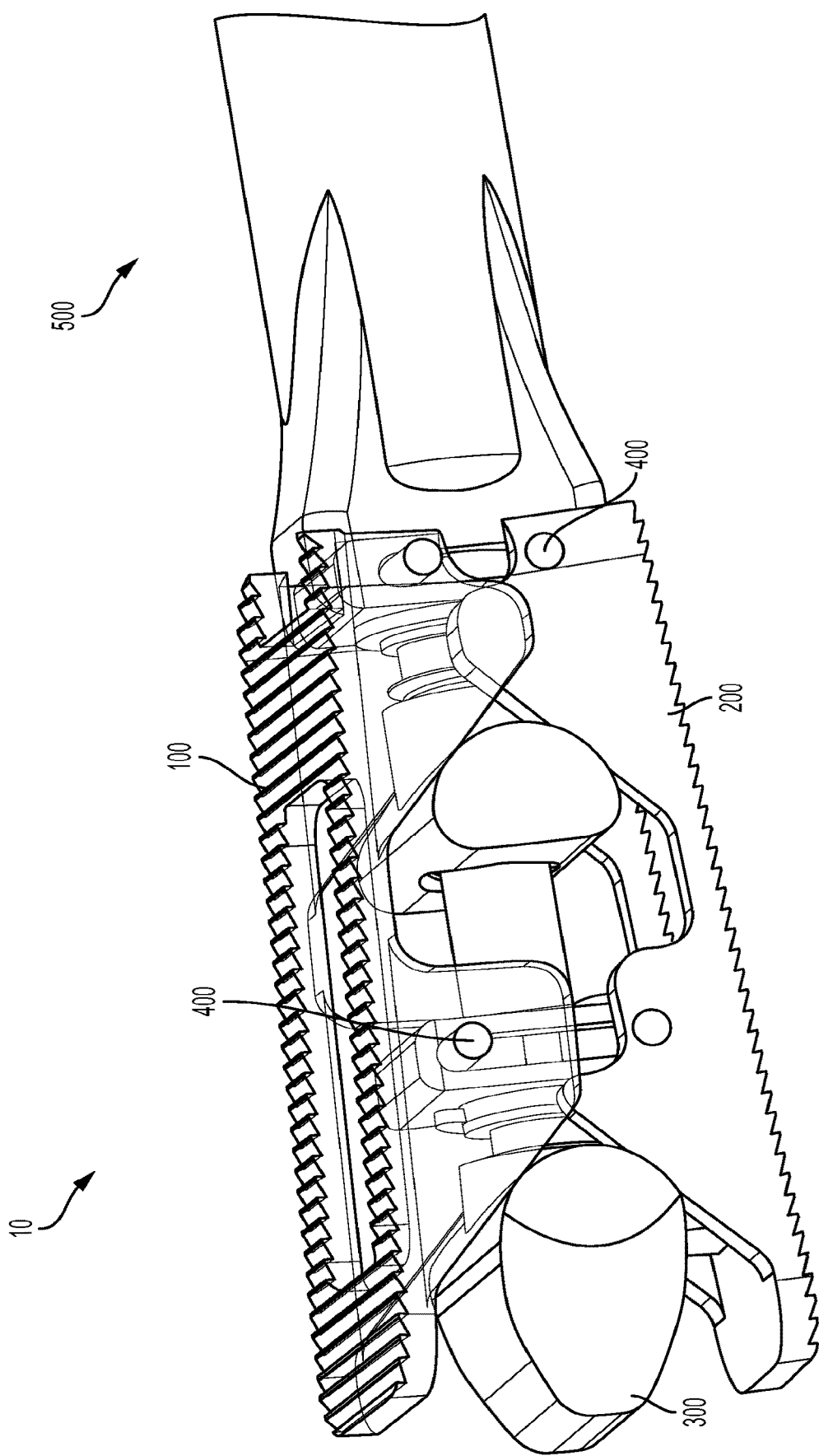
FIG. 9 is a front perspective of the inter-body fusion device of FIG. 1 in the second expanded position, in which the device angle between the first plate and the second plate is greater than 0 degrees, and in which the first plate is illustrated transparently for clarity, showing the inter-body fusion device coupled to a device driver, according to one aspect.
Figure 10:
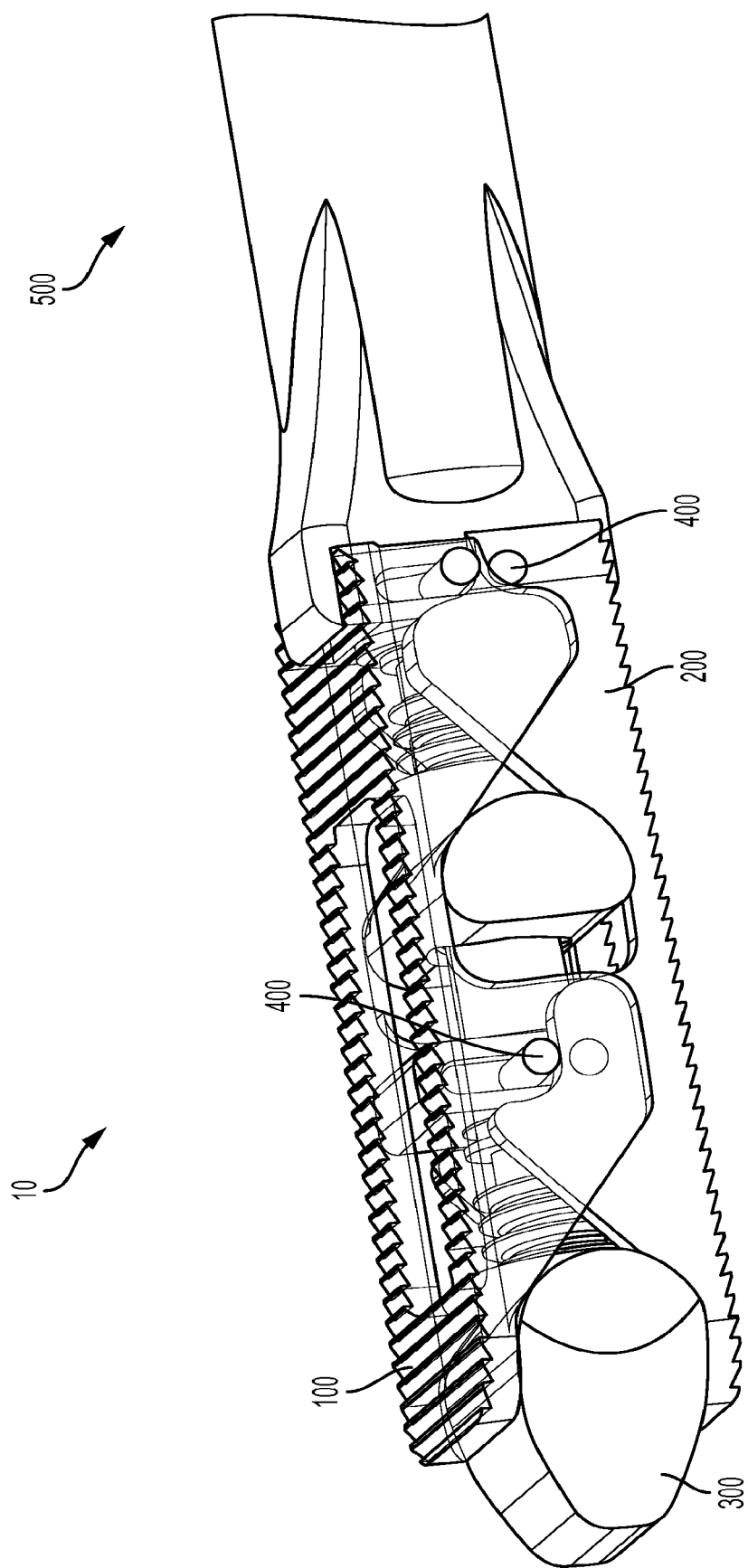
FIG. 10 is a front perspective of the inter-body fusion device of FIG. 1 in the first unexpanded position, in which the first plate is illustrated transparently for clarity, showing the inter-body fusion device coupled to a device driver, according to one aspect.
Figure 11:
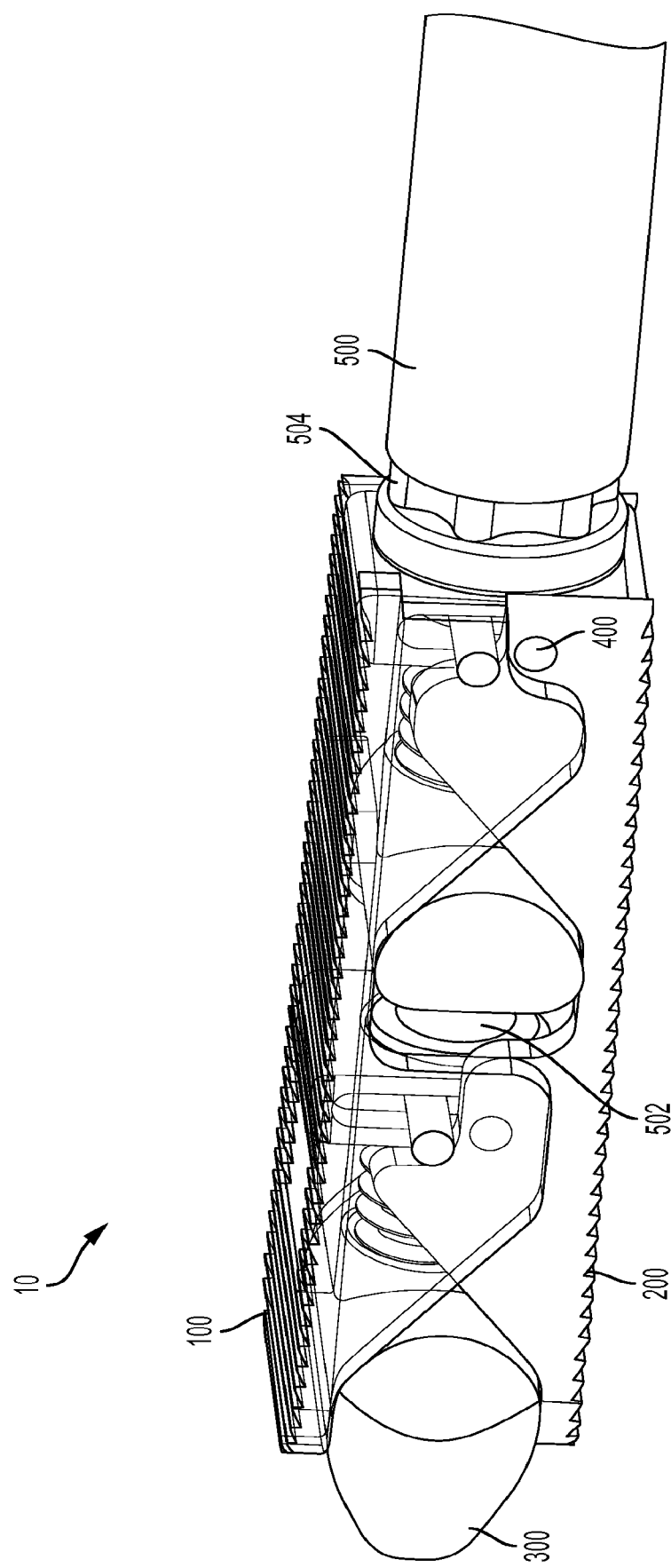
FIG. 11 is a rear perspective of the inter-body fusion device of FIG. 1 in the first unexpanded position, in which the first plate is illustrated transparently for clarity, showing the inter-body fusion device coupled to a device driver, according to one aspect
Figure 19:
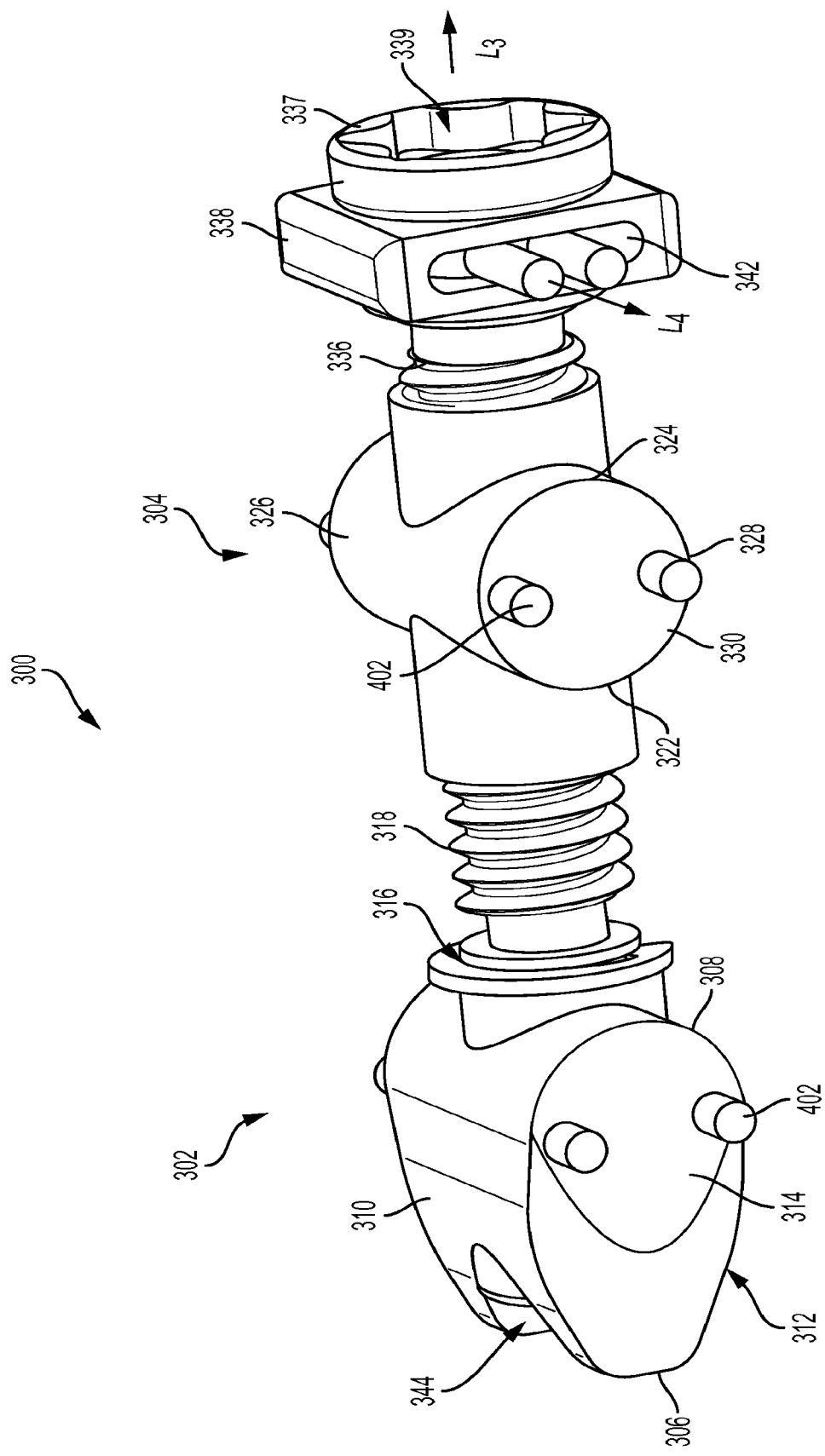
FIG. 19 is a perspective view of the insert of the inter-body fusion device of FIG. 13, according to one aspect.
Figure 20:
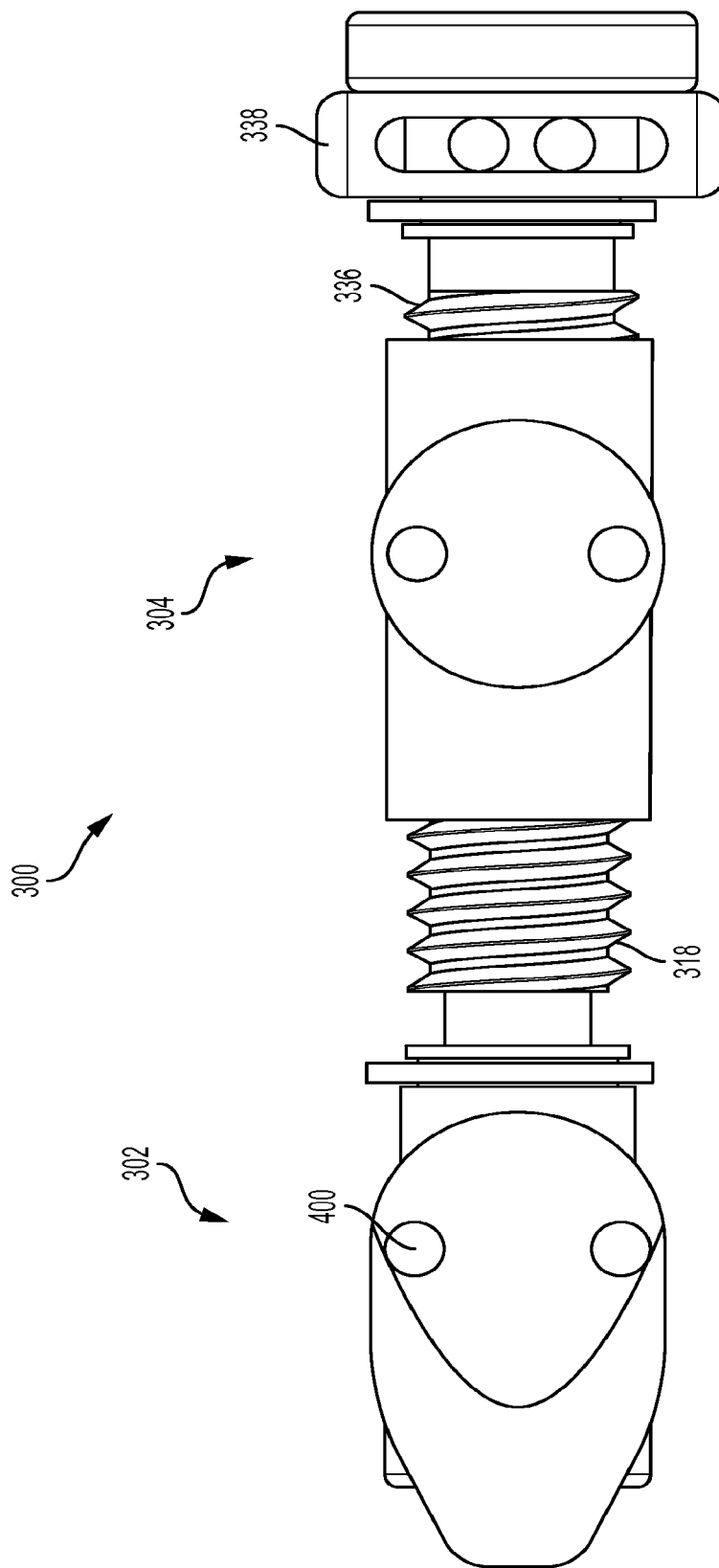
FIG. 20 is a side elevational view of the insert of FIG. 19.
Figure 26:
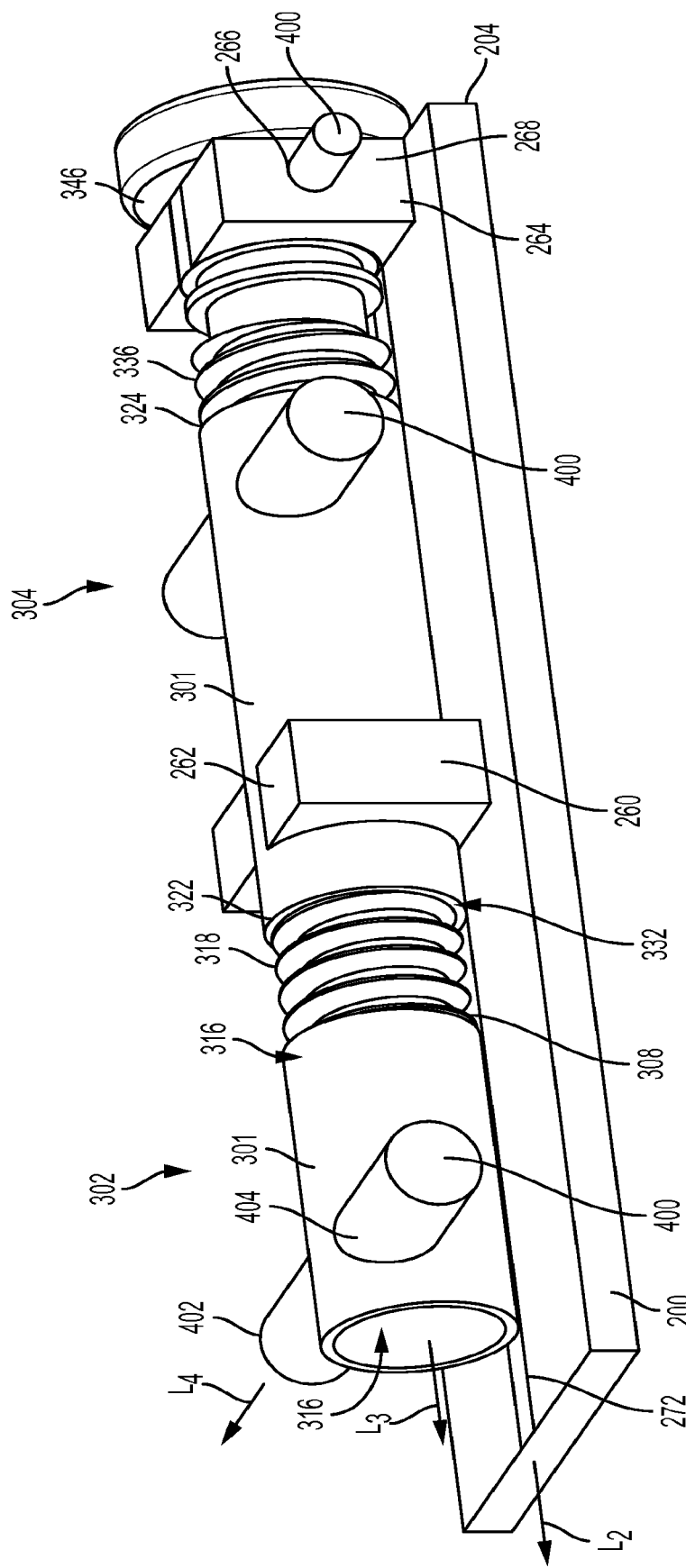
FIG. 26 is a front perspective view of the insert of the inter-body fusion device of FIG. 21, according to one aspect.
Figure 27:
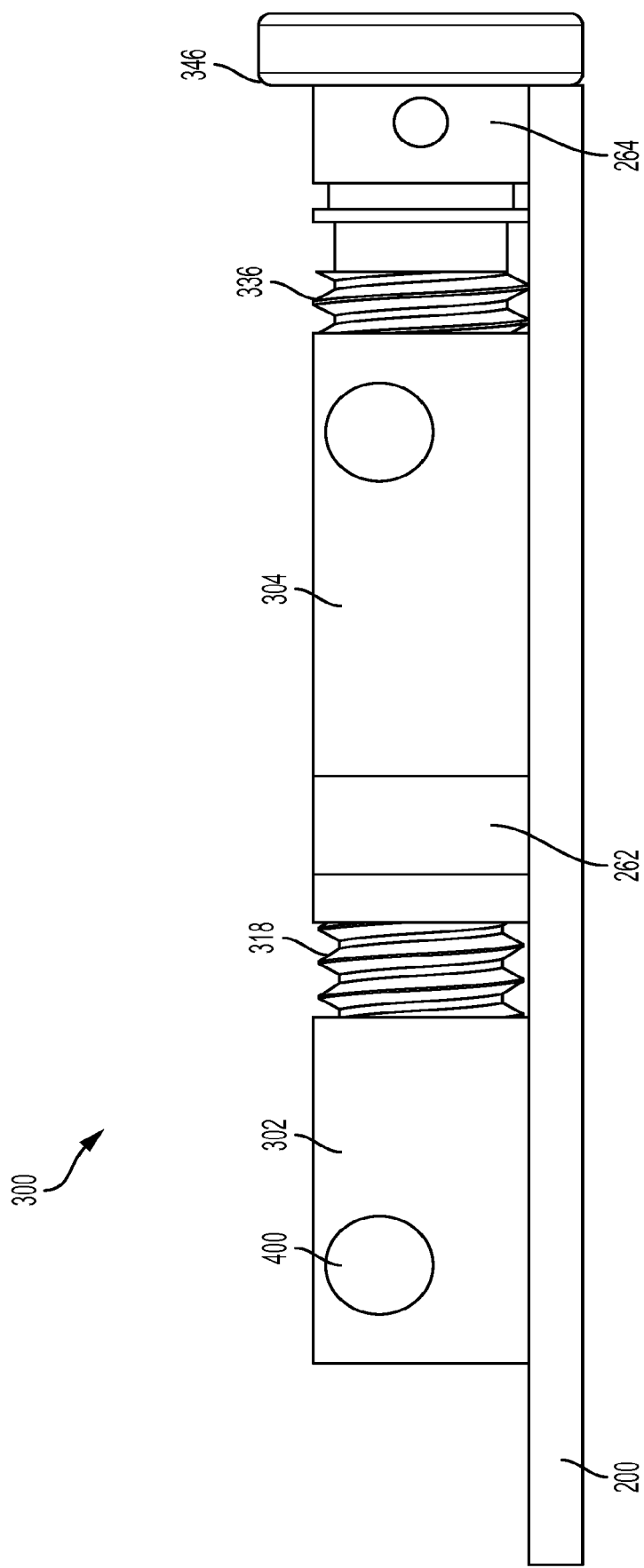
FIG. 27 is a side elevational view of the insert of FIG. 26.
Figure 28:
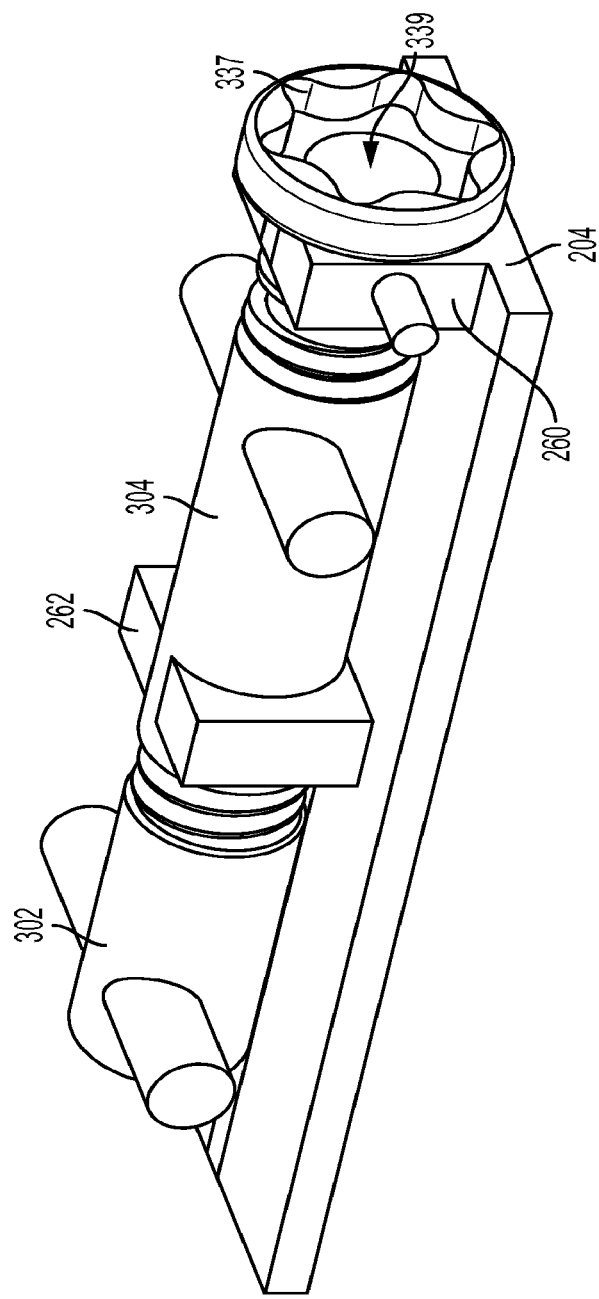
FIG. 28 is a rear perspective view of the insert of FIG. 26.

Referring now to FIGS. 5-7, in one exemplified aspect, the insert 300 comprises a first member 302 and a second member 304. In one aspect, the first member can be spaced from the second member a predetermined distance. In another aspect, the first member 302 can be physically separate from the second member 304, as in FIG. 5. Optionally, a portion of the first member can be coupled to the second member (as illustrated in FIGS. 19 and 26).

In one aspect, the first member 302 has a leading edge 306, a trailing edge 308, a first plate contact surface 310 extending between the leading edge and the trailing edge, and an opposed second plate contact surface 312 extending between the leading edge 306 and the trailing edge 308. At least one longitudinal sidewall 314 can extend substantially between the first plate contact surface and the opposed second plate contact surface. A first bore 316 can be defined in a portion of the trailing edge of the first member. In another aspect, at least a portion of the first bore can be threaded.

The first member 302 can comprise a first threaded shaft 318 and an optional first retainer 320, according to one aspect. The first retainer can be configured to couple a portion of the first member 302 to at least one of the first plate 100 and the second plate 200. In another aspect, the first threaded shaft can be coupled to a portion of the first retainer and can be configured to complementarily engage a portion of the first bore 316. Thus, rotation of the first threaded shaft 318 can cause the distance between the trailing edge 308 of the first member 302 and the first retainer to change. For example, rotation of the first threaded shaft in a first direction can make the distance between the trailing edge of the first member and the first retainer 320 smaller. In another example, rotation of the first threaded shaft 318 in a second direction that is opposed to the first direction can make the distance between the trailing edge 308 of the first member 302 and the first retainer 320 larger. A distal end 319 of the first threaded shaft can be configured to engage an actuation device, such as a screwdriver and the like so that rotation of the actuation device can rotate the first threaded shaft 318. For example, the distal end of the first threaded shaft can be slotted to engage a regular screwdriver. In another example, the distal end 319 of the first threaded shaft can be shaped to engage a hexagonal driver, and the like.

In one aspect, the second member 304 has a leading edge 322, a trailing edge 324, a first plate contact surface 326 extending between the leading edge and the trailing edge and an opposed second plate contact surface 328 extending between the leading edge 322 and the trailing edge 324. At least one longitudinal sidewall 330 can extend substantially between the first plate contact surface and the opposed second plate contact surface. A second bore 332 can extend through the second member from the leading edge to the trailing edge of the second member. In another aspect, the second bore can define a longitudinal pathway 334, and at least a portion of the second bore can be threaded. For example, the second bore 332 can extend longitudinally through the second member 304, and a portion or all of the second bore can be threaded.

The second member 304 can comprise a second threaded shaft 336 and an optional second retainer 338, according to one aspect. The second retainer can be configured to couple a portion of the second member 304 to at least one of the first plate 100 and the second plate 200. In another aspect, the second threaded shaft can be coupled to a portion of the second retainer and configured to complementarily engage a portion of the second bore 332. Thus, rotation of the second threaded shaft 336 can cause the distance between the trailing edge 324 of the second member 304 and the second retainer to change. For example, rotation of the second threaded shaft in a first direction can make the distance between the trailing edge of the second member and the second retainer 338 smaller. In another example, rotation of the second threaded shaft 336 in a second direction that is opposed to the first direction can make the distance between the trailing edge 324 of the second member 304 and the second retainer 338 larger. A distal end 337 of the second threaded shaft can be configured to engage an actuation device, such as a screwdriver and the like so that rotation of the actuation device can rotate the second threaded shaft 336. For example, the distal end of the second threaded shaft can be slotted to engage a regular screwdriver. In another example, the distal end 337 can be shaped to engage a hexagonal driver, and the like. In one aspect, a longitudinal duct 339 can be defined therethrough the second threaded shaft. In use, the longitudinal duct of the second threaded shaft can be substantially coaxially aligned with the longitudinal pathway 334 of the second member so that at least a portion of the actuation device can be inserted through both the longitudinal duct 339 of the second threaded shaft 336 and the longitudinal pathway 334 of the second member 304. A shoulder 346 of the second threaded shaft can engage a portion of the second retainer 338 to restrict longitudinal movement of the second threaded shaft 336.

In one aspect, portions of the first plate contact surfaces 310, 326 of the first member 302 and/or the second member 304 can be configured to engage the inner surface 120 of first plate 100 of the device 10. In another aspect, portions of the second plate contact surfaces 312, 328 of the first member 302 and/or the second member 304 can be configured to engage the inner surface 220 of the second plate 200. For example, portions of the first plate contact surface 310 of the first member can be configured to engage the upper flat surface 138 and/or the first inclined surface 140 of the first plate, and portions of the first plate contact surface 326 of the second member 304 can be configured to engage the upper flat surface 138 and/or the second inclined surface 144 of the first plate 100. In another example, portions of the second plate contact surface 312 of the first member 302 can be configured to engage the lower flat surface 238 and/or the first inclined surface 240 of the second plate 200, and portions of the second plate contact surface 328 of the second member 304 can be configured to engage the lower flat surface 238 and/or the second inclined surface 244 of the second plate. As seen in the FIGS. 1-4, the inclined surfaces of the first and second plates can cooperate with the flat surfaces 136, 236 to cam or wedge the first plate 100 and/or the second plate 200 to a desired position and orientation relative to each other based on the position of the first member 302 and the second member 304 relative to the plates.

The inter-body fusion device 10 can further comprise at least one pin 400 configured to couple a portion of the insert 300 to at least one of the first plate 100 and the second plate 200. For example and as illustrated in FIGS. 1-5, a proximal end 402 of each pin can be formed with or securely attached to the pin bore 146 of the longitudinal sidewall 130 of the first plate and/or the pin bore 246 of the longitudinal sidewall 230 of the second plate such that a distal end 404 of the pin 400 extends from the sidewall into the interior cavity 15 of the device 10. In one aspect, at least one pin can be positioned such that a longitudinal axis L4 of the pin is substantially transverse to the longitudinal axis of the first plate Li. In one aspect, the distal end of each pin can be configured to slidingly engage a first slot 340 defined in the first retainer 320 and/or a second slot 342 defined in the second retainer 338 of the insert 300. In another aspect, the first slot and/or the second slot can be substantially transverse to a longitudinal axis L3 of the insert. Optionally, however, the first slot 340 and/or the second slot 342 can be at an acute angle relative to the longitudinal axis L3 of the insert.

To assemble the inter-body fusion device 10, the insert 300 can be positioned between the first plate 100 and the second plate 200 such that the leading edge 306 of the insert, the leading edge 102 of the first plate, and the leading edge 202 of the second plate are facing the same direction. In one aspect, portions of the first plate 100 can overlie the second plate 200. Correspondingly, in one aspect, each longitudinal sidewall 130 of the first plate 100 can substantially align with a longitudinal sidewall 230 of the second plate 200. For example, each longitudinal sidewall of the first plate can substantially overlie at least a portion of a longitudinal sidewall of the second plate. Optionally, each longitudinal sidewall 130 of the first plate 100 can be positioned adjacent to at least a portion of a longitudinal sidewall 230 of the second plate 200 so that the inner surface 120 of the first plate and the inner surface 220 of the second plate do not contact each other. The proximal end 402 of the at least one pin 400 can be coupled to the longitudinal sidewall of at least one of the first and second plate and the distal end 404 of the pin can extend into the first slot 340 or the second slot 342 of the insert 300. Thus, when assembled, a portion of pin can slide in the slot and allow the first plate 100, the second plate 200, and/or the insert to move relative to each other in the direction of the slot.

Figure 2:
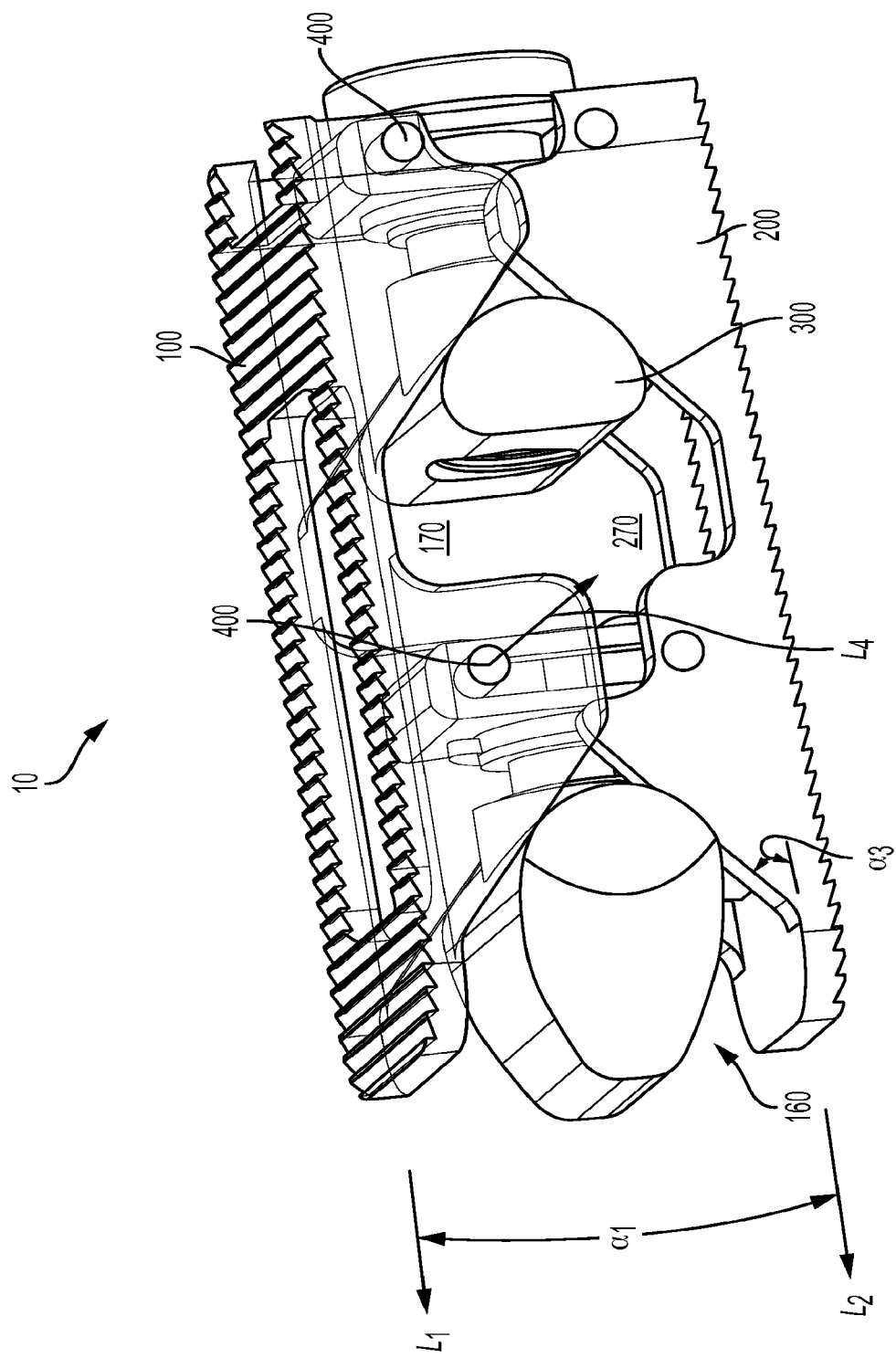
FIG. 2 is a front perspective of the inter-body fusion device of FIG. 1 in the second expanded position, in which a device angle between the first plate and the second plate is substantially 0 degrees (the first plate and the second plate are substantially parallel), and in which the first plate is illustrated transparently for clarity.
Figure 3:
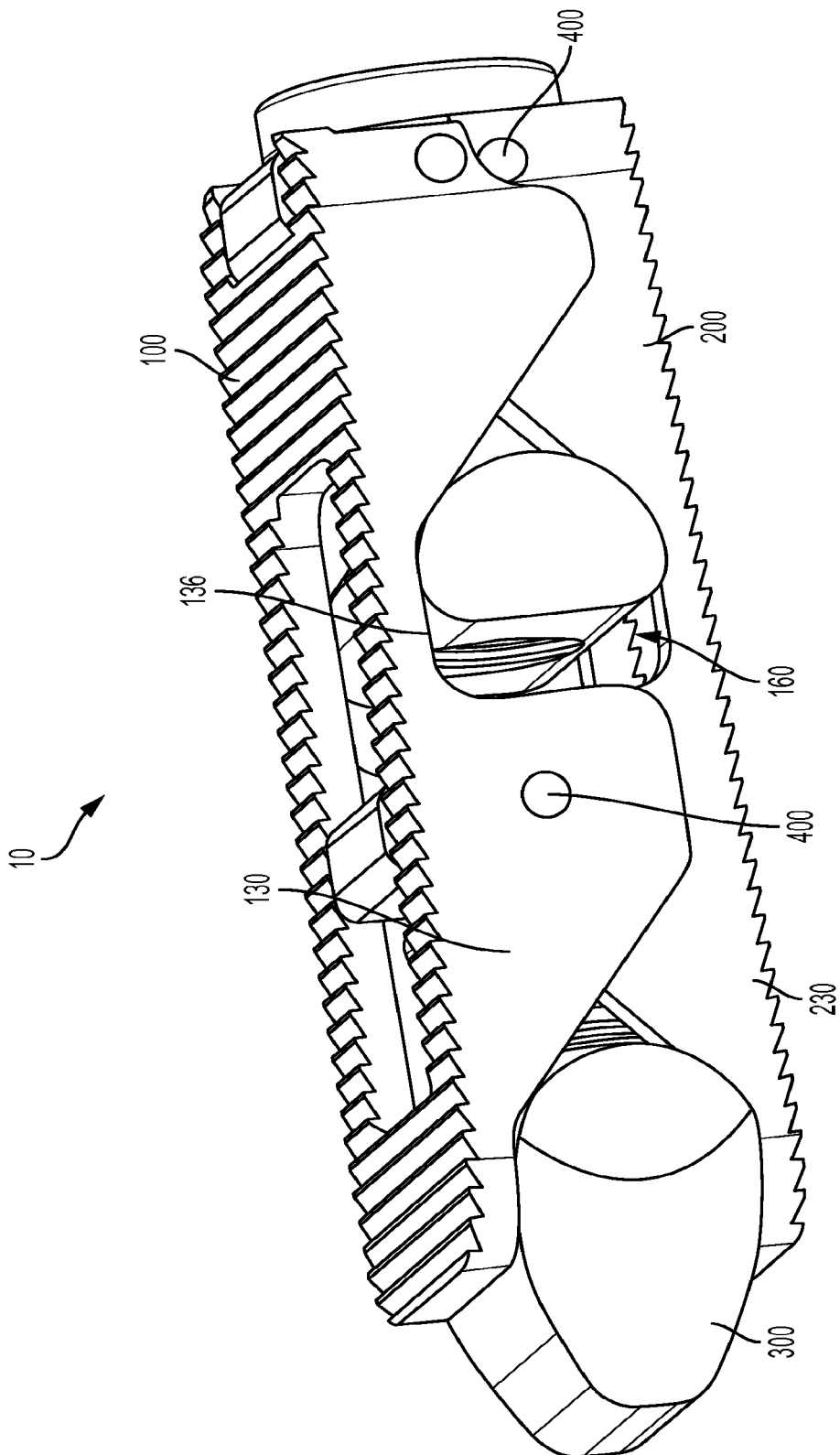
FIG. 3 is a front perspective of the inter-body fusion device of FIG. 1 in a first unexpanded position.
Figure 4:
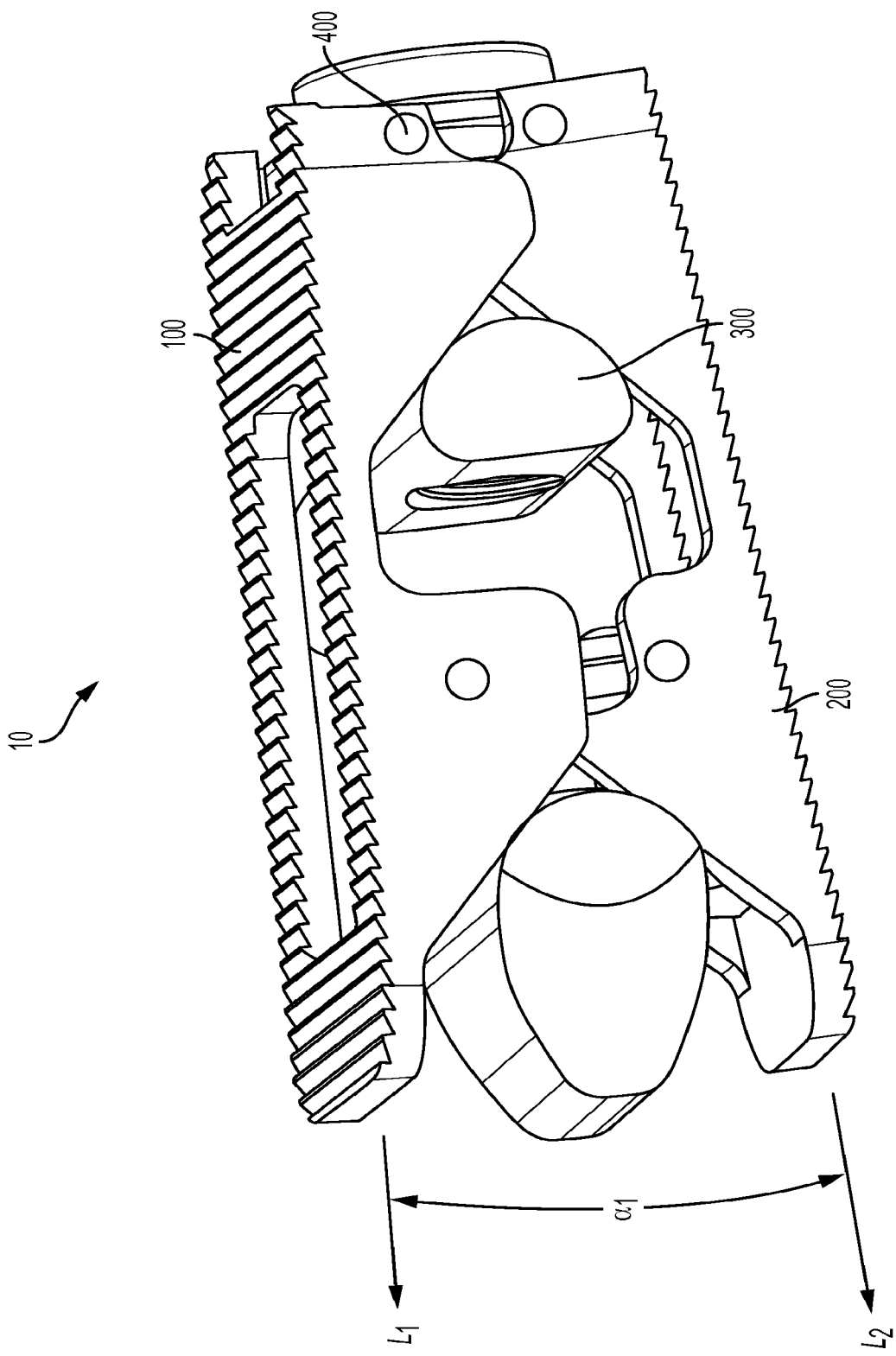
FIG. 4 is a front perspective of the inter-body fusion device of FIG. 1 in the second expanded position, and in which the device angle between the first plate and the second plate is greater than 0 degrees.

Each set of substantially aligned longitudinal sidewalls (a longitudinal sidewall 130 from the first plate 100 and a longitudinal sidewall 230 from the second plate 200) define at least one void 160, as illustrated in FIGS. 1 and 2. In another aspect, the at least one void can be sized and shaped to complimentarily accept a portion of the first member 302 or the second member 304 of the insert 300 therein. In this aspect, in a first unexpanded position (as illustrated in FIG. 3), each of the first member and the second member of the insert 300 can be positioned substantially within the void 160 formed between the substantially aligned longitudinal sidewalls 130, 230 of the first and second plates 100, 200. In the first unexpanded position, at least one of the first member 302 and the second member 304 can be positioned in the void substantially near or in contact with the respective flat surface 136, 236 of the first and second plates. Note that the first unexpanded position is the position in which the inter-body fusion device 10 can be inserted between the adjacent vertebrae of a patient.

The inter-body fusion device 10 can be selectively expanded about and between the first unexpanded position, in which a portion of the first member 302 and/or the second member 304 of the insert 300 can be positioned substantially near or in contact with the respective flat surface 136, 236 of the first and second plates, and a second expanded position in which a portion of the first member 302 and/or the second member 304 of the insert 300 can be positioned substantially near or in contact with the respective inclined surface 134, 234 of the first and second plates 100, 200. That is, in the second expanded position, the first member and/or the second member can be spaced from the respective flat surface 136, 236 of the first and second plates a predetermined distance. As can be appreciated, in the second expanded position, the inter-body fusion device 10 can have a height and interior cavity 15 volume that is greater than the height and interior cavity volume of the inter-body fusion device in the first, unexpanded position. Thus, in the first unexpanded position, the interior cavity 15 of the device can have a first cavity size, and in the second expanded position the interior cavity can have a second cavity size that is greater than the first cavity size.

In one aspect, in the first, unexpanded position, the longitudinal axis $L_1$ of the first plate 100 and the longitudinal axis $L_2$ of the second plate 200 can be substantially parallel to each other or, optionally, the longitudinal axis $L_1$ of the first plate and the longitudinal axis $L_2$ of the second plate can be at an acute angle relative to each other. In another aspect, in the second, expanded position, the longitudinal axis $L_1$ of the first plate 100 and the longitudinal axis $L_2$ of the second plate 200 can be substantially parallel to each other or, optionally, the longitudinal axis $L_1$ of the first plate and the longitudinal axis $L_2$ of the second plate can be at an acute angle relative to each other.

In order to selectively expand the inter-body fusion device 10 about and between the first unexpanded position and the second expanded position, at least the one of the first member 302 or the second member 304 of the insert 300 can be moved longitudinally about and between a first insert position and a second insert position. In one aspect, in the first insert position, the trailing edge 308 of the first member can be spaced from the trailing edge 104 of the first plate 100 an unexpanded first distance, and the trailing edge 324 of the second member can be spaced from the trailing edge 104 of the first plate 100 an unexpanded second distance. In the second insert position, the trailing edge 308 of the first member can be spaced from the trailing edge 104 of the first plate 100 an expanded first distance that is less than the unexpanded first distance, and the trailing edge 324 of the second member can be spaced from the trailing edge 104 of the first plate 100 an expanded second distance that is less than the unexpanded second distance.

In moving the inter-body fusion device 10 about and between the first unexpanded position and the second expanded position, the first member 302 and the second member 304 of the insert 300 do not necessarily need be moved simultaneously or to the same insert position. For example, the first member can be in the first insert position while the second member can be in the second insert position. In another example, the first member 302 can be in the second insert position while the second member 304 can be in the first insert position. Thus, the first member and the second member can be in any insert position between the first insert position and the second insert position at any time regardless of the position of the other member.

Upon moving the first member 302 towards the second insert position, at least a portion of the first plate contact surface 310 can be moved into contact with the first inclined surface 140 of the longitudinal sidewall 130 of the first plate 100, and at least a portion of the second plate contact surface 312 can be moved into contact with the first inclined surface 240 of the longitudinal sidewall 230 of the second plate 200. In this position, the aligned longitudinal sidewalls of the first and second plates 100, 200 are separated by the first member traveling over the inclined surfaces 140, 240 to cam the plates away from each other.

Similarly, upon moving the second member 304 towards the second insert position, at least a portion of the first plate contact surface 326 can be moved into contact with the second inclined surface 144 of the longitudinal sidewall 130 of the first plate 100, and at least a portion of the second plate contact surface 328 can be moved into contact with the second inclined surface 244 of the longitudinal sidewall 230 of the second plate 200. In this position, the aligned longitudinal sidewalls of the first and second plates 100, 200 are separated by the second member traveling over the inclined surfaces 144, 244 to cam the plates away from each other.

As one skilled in the art can appreciate, the amount of separation achievable between the first plate 100 and the second plate 200 can be determined by the height of the inclined surfaces and the distance of longitudinal movement of the second member. Further, the angle formed between the first plate and the second plate can be determined by at least the position of the first member 302 of the insert relative to the second member 304.

It is contemplated that this technology can be used for a variety of implants used for a variety of spinal procedures. As mentioned before, these procedures include, but are not limited to OLIF, DLIF, PLIF, ALIF, TLIF, and LLIF. Because of this, depending upon the procedure and point of insertion for the implant, the geometry of the implant can differ. For example, in a DLIF expandable device, the approach is lateral. As such, the upper bone contact surface 110 can be transversely angled with respect to the lower bone contact surface 210 from a first sidewall to a second sidewall to match, increase, or decrease lordosis.

In an OLIF procedure, the inter-body fusion device 10 can be inserted obliquely, either anteriorly or posteriorly. As such, similar to the DLIF implant, the upper bone contact surface 110 can be angled transversely with respect to the lower bone contact surface 210 from the first sidewall to the second sidewall depending on the need to match, increase, or decrease lordosis. In addition, the upper bone contact surface can also be angled longitudinally with respect to the lower bone contact surface from the leading end 20 of the device to the trailing end 30.

In an exemplified aspect, at least one of the first plate 100 and the second plate 200 can define at least one graft window 170, 270 that is in communication with the interior cavity 15. The at least one graft window 170 defined in the first plate can overlie at least a portion of the at least one graft window 270 of the second plate, thereby permitting bone growth therethrough. In another aspect, the upper bone contact surface 110 of the first plate 100 comprises ridges 112 for frictionally engaging a first vertebra of the patient. As can be appreciated, the lower bone contact surface 210 of the second plate can comprise ridges 212 to frictionally engage a second vertebra of the patient.

Figure 12:
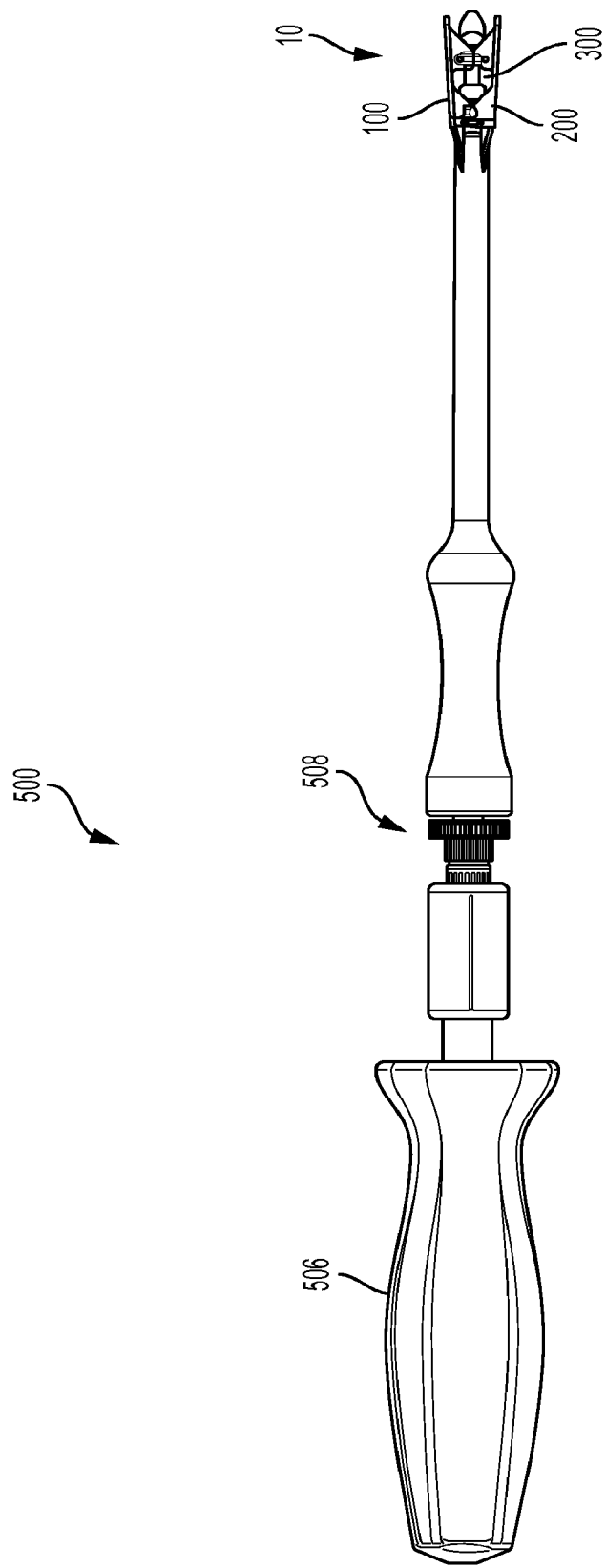
FIG. 12 is side elevational of the device driver of FIG. 9, showing the device driver coupled to the inter-body fusion device of FIG. 1, according to one aspect.

In one aspect, as shown in FIGS. 8-12, the inter-body fusion device 10 can be actuated by a device driver 500. The device driver can comprise a first member driver 502 sized and shaped to engage the distal end 319 of the first threaded shaft 318, and a second member driver 504 sized and shaped to engage the distal end 337 of the second threaded shaft 336. In another aspect, the first member driver can be a separate tool than the second member driver. Optionally, however, the first member driver 502 and the second member driver 504 can be integrally formed as illustrated in FIG. 12. For example, the device driver 500 can further comprise a handle 506 and a clutch collar 508 that allows the device driver to be adjustable between an engaged position and a disengaged position. In the engaged position, the clutch collar can couple the first member driver 502 to the second member driver 504 so that, upon rotation of the handle, both the first member driver and the second member driver rotate at the same speed as the handle. In the disengaged position, the clutch collar 508 can disengage the first member driver 502 from the second member driver 504 so that upon rotation of the handle 506, either the first member driver or the second member driver can rotate at the same speed as the handle while the disengaged driver does not rotate.

In use, the first member driver 502 can be inserted through the longitudinal duct 339 of the second threaded shaft 336 and through the longitudinal pathway 334 of the second member 304 so that the first member driver can be coupled to the distal end 319 of the first threaded shaft 318 of the first member. The second member driver can be coupled to the distal end 337 of the second member. A gripping element 510 of the device driver can grip at least a portion of the inter-body fusion device 10, such as, the first plate 100, the second plate, or as illustrated in the figures, the second retainer 338 of the insert 300. The clutch collar 508 of the device driver can be placed in the engaged position, and the handle 506 of the device driver can be rotated. For example, if the inter-body fusion device is in the first, unexpanded position, rotation of the handle can cause the first member 302 and the second member 304 of the insert to move from the first insert position towards the second insert position. As the first member and the second member move towards the second insert position, the first plate 100 and the second plate 200 are urged away from each other, and the height of the device increases. In another example, if the inter-body fusion device is in the second expanded position, rotation of the handle can cause the first member 302 and the second member 304 of the insert to move from the second insert position towards the first insert position. As the first member and the second member move towards the first insert position, the first plate 100 and the second plate 200 are can move towards each other, and the height of the device decreases.

When the desired device height has been reached, the clutch collar can be moved to the disengaged position. In the disengaged position, rotation of the handle can cause only one of the first member 302 and the second member 304 to move. For example, rotation of the handle in a first direction can cause the first member 302 to move longitudinally towards the trailing edge 104 of the first plate, thereby increasing the angle between the longitudinal axis of the first plate and the second plate (the device angle). In another example, rotation of the first member driver 502 in a second direction that is opposed to the first direction can cause the first member 302 to move longitudinally towards the leading edge 102 of the first plate 100, thereby decreasing the device angle. When the desired device angle has been reached, the device driver 500 can be removed from the device 10.

A second embodiment of the inter-body fusion device 10 is illustrated in FIGS. 13-20, according to one aspect. In this embodiment, the inter-body fusion device can be as described above, comprising a first plate 100, a second plate 200, and an insert 300. Optionally, however, the insert can be a continuous insert. That is, a portion of the first member 302 of the insert 300 can be coupled to the second member 304 as illustrated in FIG. 19. In one aspect, the first threaded shaft 318 of the first member can be configured to matingly engage a portion of the second bore 332 of the second member such that rotation of the first threaded shaft can move the first member 302 longitudinally relative to the second member 304. Thus, rotation of the first threaded shaft 318 can cause the distance between the trailing edge 308 of the first member and the leading edge 322 of the second member to change. For example, rotation of the first threaded shaft in a first direction can make the distance between the trailing edge of the first member 302 and the leading edge of the second member 304 smaller. In another example, rotation of the first threaded shaft 318 in a second direction that is opposed to the first direction can make the distance between the trailing edge 308 of the first member and the leading edge of the second member 304 larger.

Referring still to FIG. 19, a notch 344 can be defined in a portion of the first member 302, such as, for example, in the first plate contact surface 310 and/or the second plate contact surface 312. In one aspect, the notch can be in communication with the first bore 316 so that the first threaded shaft 318 can be inserted through the notch and into the first bore in a direction from the leading edge 306 to the trailing edge 308 of the first member. In another aspect, the first threaded shaft can be inserted through the notch and through the first bore so that at least a portion of the distal end 319 of the first threaded shaft 318 can engage the threads of the second bore 332 of the second member 304.

The at least one pin 400 can comprise a plurality of pins. In one aspect, at least one pin of the plurality of pins can be coupled to or formed integrally with the first member 302 and/or the second member 304 of the insert. In another aspect, the distal end 404 of the at least one pin can be securely attached to or formed integrally with the longitudinal sidewall 314, 330 of the respective first member and/or second member. The proximal end 402 of the pin can extend away from the longitudinal sidewall and be configured to engage at least one slot 148, 248 defined in at least one of respective first plate 100 and the second plate 200. In another aspect, at least one pin can be positioned such that a longitudinal axis of the pin $L_4$ is substantially transverse to the longitudinal axis of the insert $L_3$.

Figure 13:
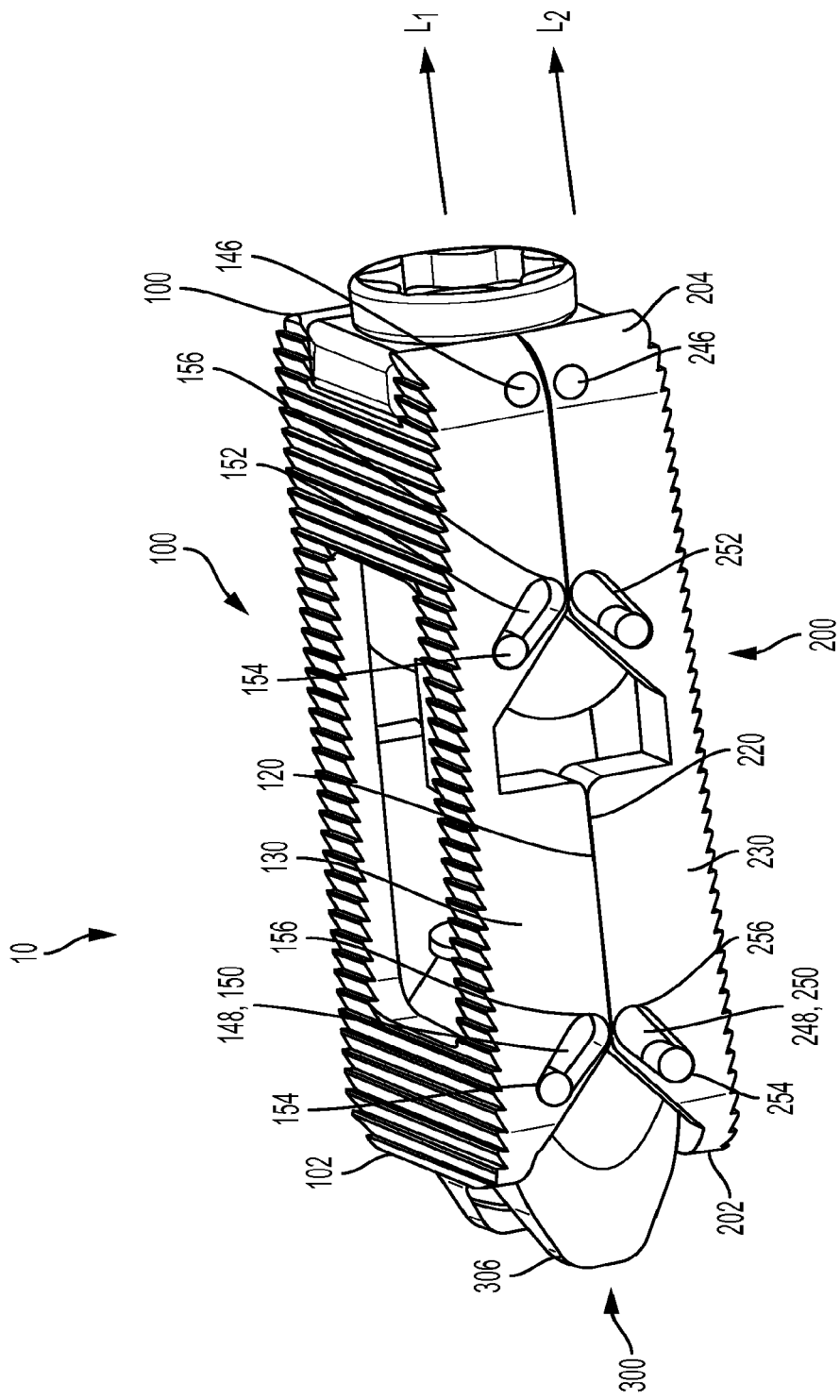
FIG. 13 is a front perspective view of a second embodiment of an expandable, adjustable inter-body fusion device in a first unexpanded position, the device comprising a first plate, a second plate and an insert, according to one aspect.
Figure 14:
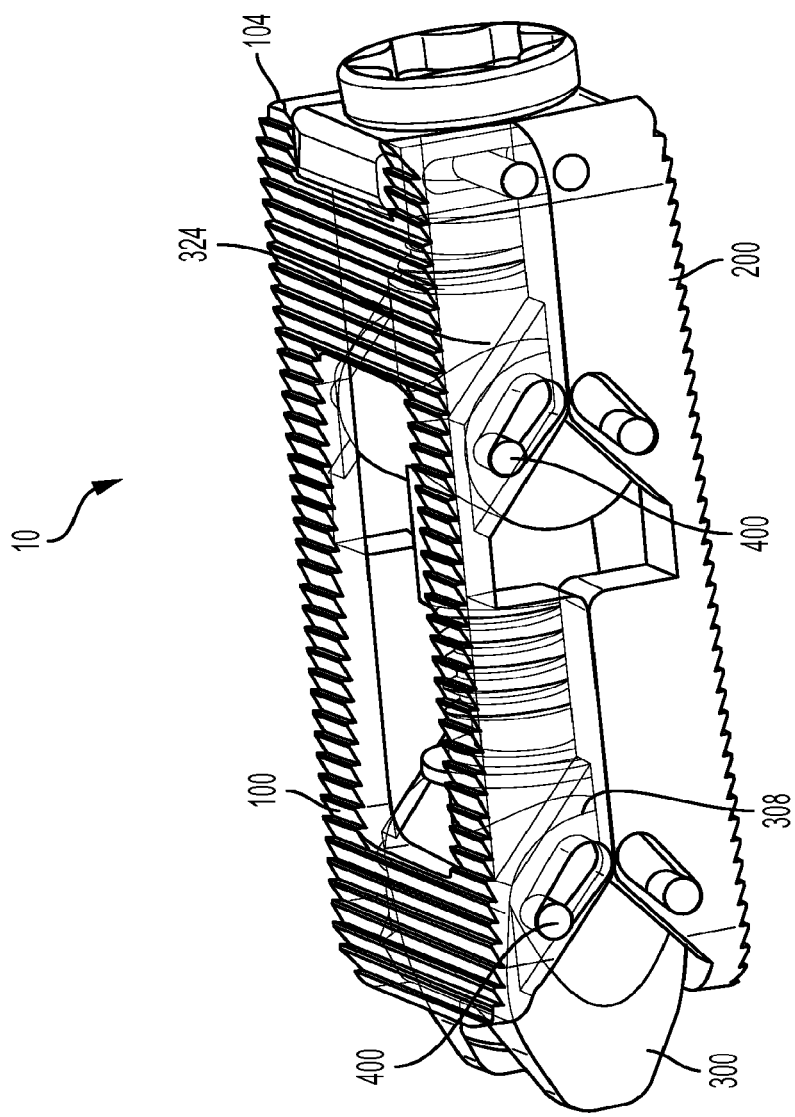
FIG. 14 is a perspective view of the inter-body fusion device of FIG. 13 in the first unexpanded position, in which the first plate is illustrated transparently for clarity.

With reference now to FIG. 13, the at least one slot 148 can be defined in the longitudinal sidewall 130 of the first plate 100 along a slot axis $L_5$. In one aspect, the at least one slot of the first plate can comprise a plurality of slots, such as, for example and without limitation, a third slot 150 and a fourth slot 152. Each slot can have a leading end 154 and a trailing end 156, the leading end being positioned closed to the upper bone contact surface 110 of the first plate than the trailing end. In another aspect, the third slot and/or the fourth slot can be positioned along the slot axis $L_5$ that is substantially transverse to the longitudinal axis $L_1$ of the first plate 100. Optionally, however, the slot axis $L_5$ of the third slot 150 and/or the fourth slot 152 can be at an acute slot angle relative to the longitudinal axis $L_1$ of the first plate. In another aspect, the third slot and/or the fourth slot can be substantially parallel to each other. The third slot 150 can be sized, shaped and positioned to engage the proximal end 402 of a pin 400 coupled to the first member 302, and the fourth slot can be sized, shaped and positioned to engage the proximal end of a pin coupled to the second member 304.

Similarly, at least one slot 248 can be defined in the longitudinal sidewall 230 of the second plate 200. In one aspect, the at least one slot of the second plate can comprise a fifth slot 250 and a sixth slot 252. Each slot of the at least one slot can have a leading end 254 and a trailing end 256, the leading end being positioned closed to the lower bone contact surface 210 than the trailing end. In another aspect, the fifth slot and/or the sixth slot can be positioned along the slot axis $L_5$ that is substantially transverse to the longitudinal axis $L_2$ of the second plate 200. Optionally, however, the slot axis of the fifth slot 250 and/or the sixth slot 252 can be at an acute slot angle relative to the longitudinal axis $L_2$ of the second plate. In another aspect, the fifth slot and/or the sixth slot can be substantially parallel to each other. The fifth slot 250 can be sized, shaped and positioned to engage the proximal end 402 of a pin 400 coupled to the first member 302, and the sixth slot can be sized, shaped and positioned to engage the proximal end of a pin coupled to the second member 304.

To assemble the inter-body fusion device 10 according to this embodiment, the insert 300 can be positioned between the first plate 100 and the second plate 200 such that the leading edge 306 of the insert, the leading edge 102 of the first plate, and the leading edge 202 of the second plate are facing the same direction. In one aspect, portions of the first plate 100 can overlie the second plate 200. Correspondingly, in one aspect, each longitudinal sidewall 130 of the first plate 100 can substantially align with a longitudinal sidewall 230 of the second plate 200. For example, each longitudinal sidewall of the first plate can substantially overlie at least a portion of a longitudinal sidewall of the second plate. Optionally, each longitudinal sidewall 130 of the first plate 100 can be positioned adjacent to at least a portion of a longitudinal sidewall 230 of the second plate 200 so that at least a portion of the inner surface 120 of the first plate and the inner surface 220 of the second plate can contact each other.

The proximal end 402 of a pin 400 can be coupled to the longitudinal sidewall 130 of the first plate 100 adjacent to the trailing edge 104, and the proximal end of a pin can be coupled to the longitudinal sidewall 230 of the second plate 200 adjacent to the trailing edge 204 so that the distal end 404 of each pin can extend into the second slot 342 of the second retainer 338 of the insert 300. Thus, when assembled, a portion of pin can slide in the second slot and allow the first plate 100, the second plate 200, and/or the insert to move relative to each other.

Figure 15:
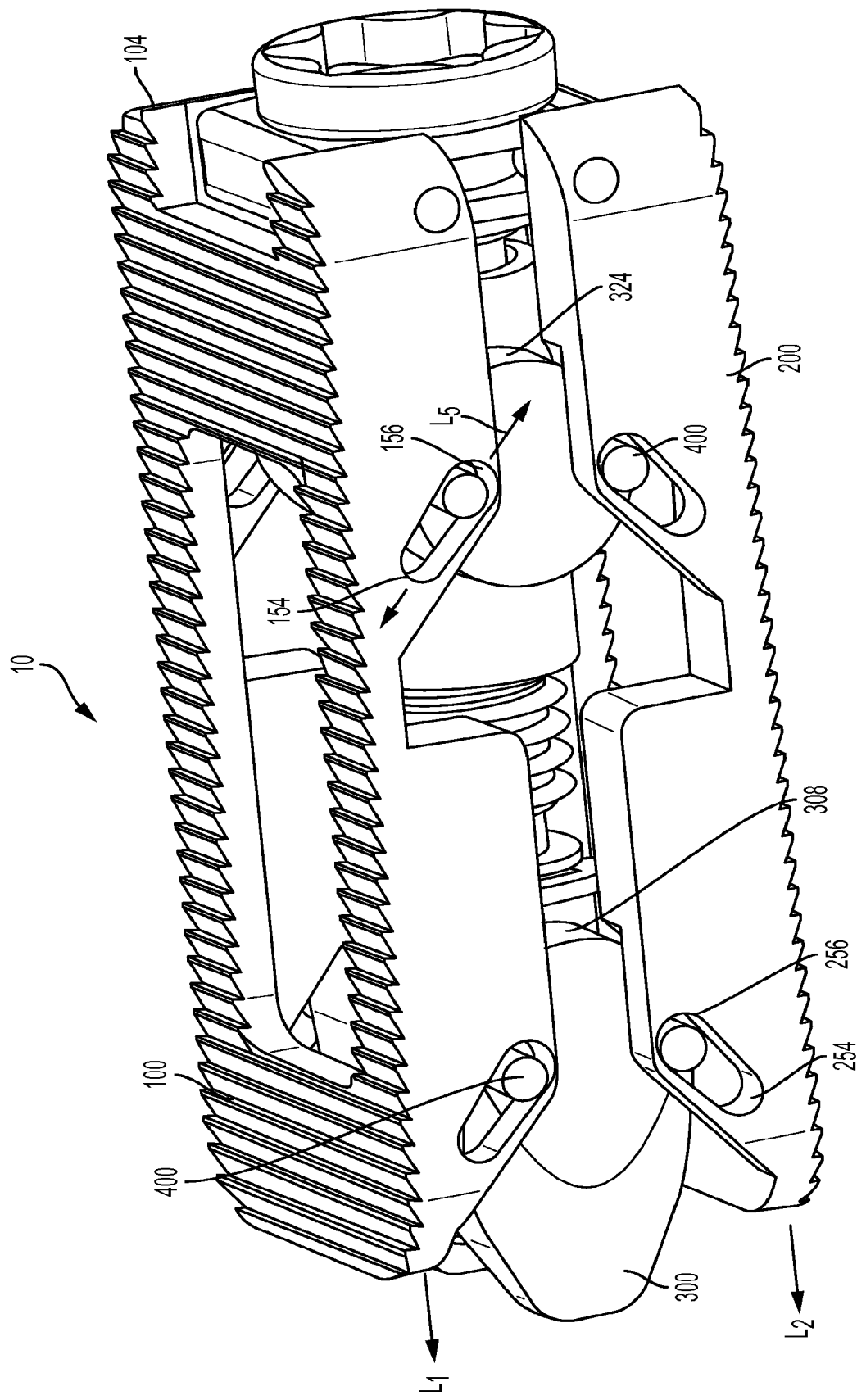
FIG. 15 is a perspective view of the inter-body fusion device of FIG. 13 in a second expanded position in which the device angle between the first plate and the second plate is substantially 0 degrees.
Figure 16:
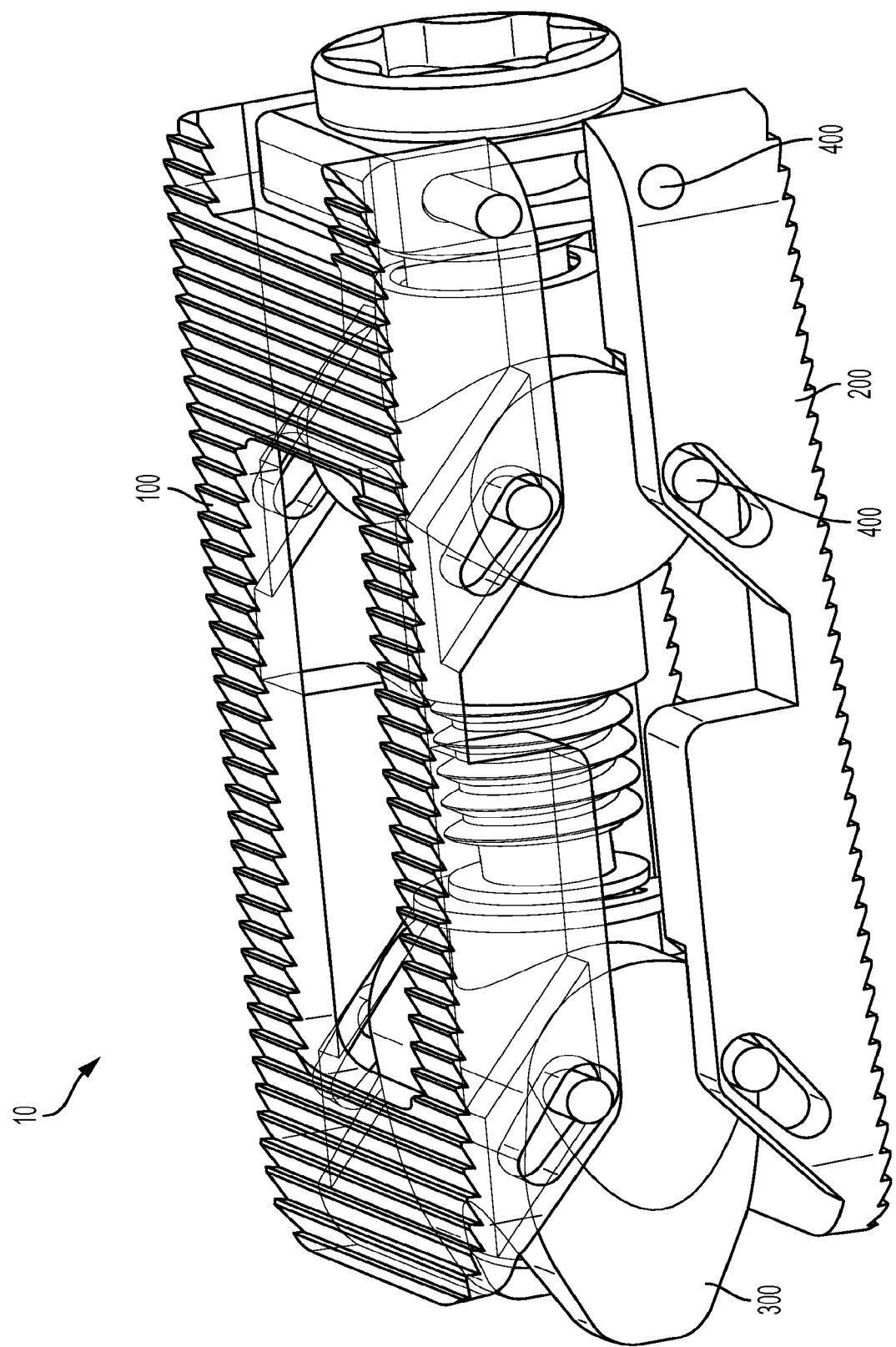
FIG. 16 is a perspective view of the inter-body fusion device of FIG. 13 in the second expanded position in which the device angle between the first plate and the second plate is substantially 0 degrees and in which the first plate is illustrated transparently for clarity.
Figure 17:
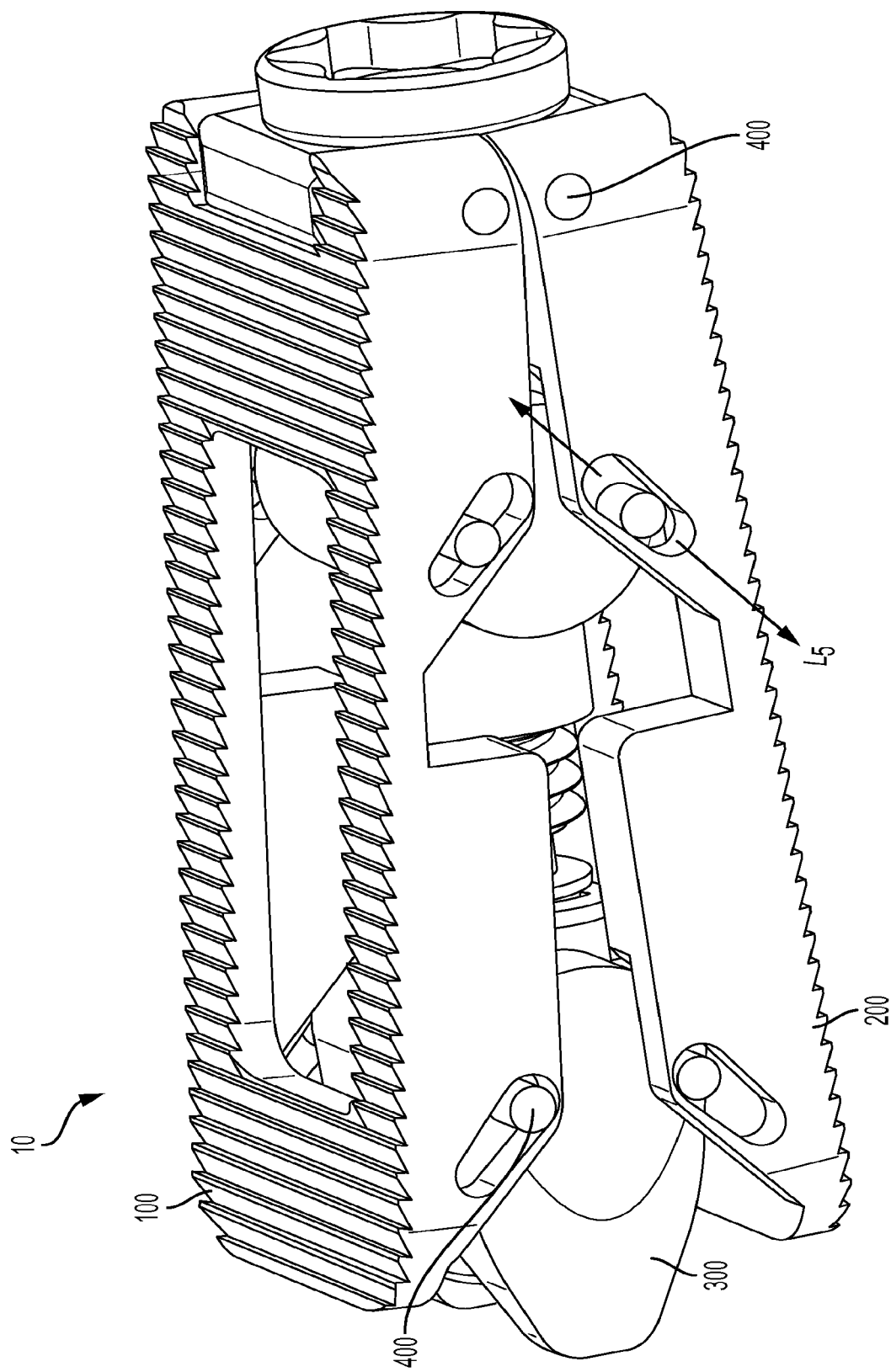
FIG. 17 is a perspective view of the inter-body fusion device of FIG. 13 in the second expanded position and in which the device angle between the first plate and the second plate is greater than 0 degrees.
Figure 18:
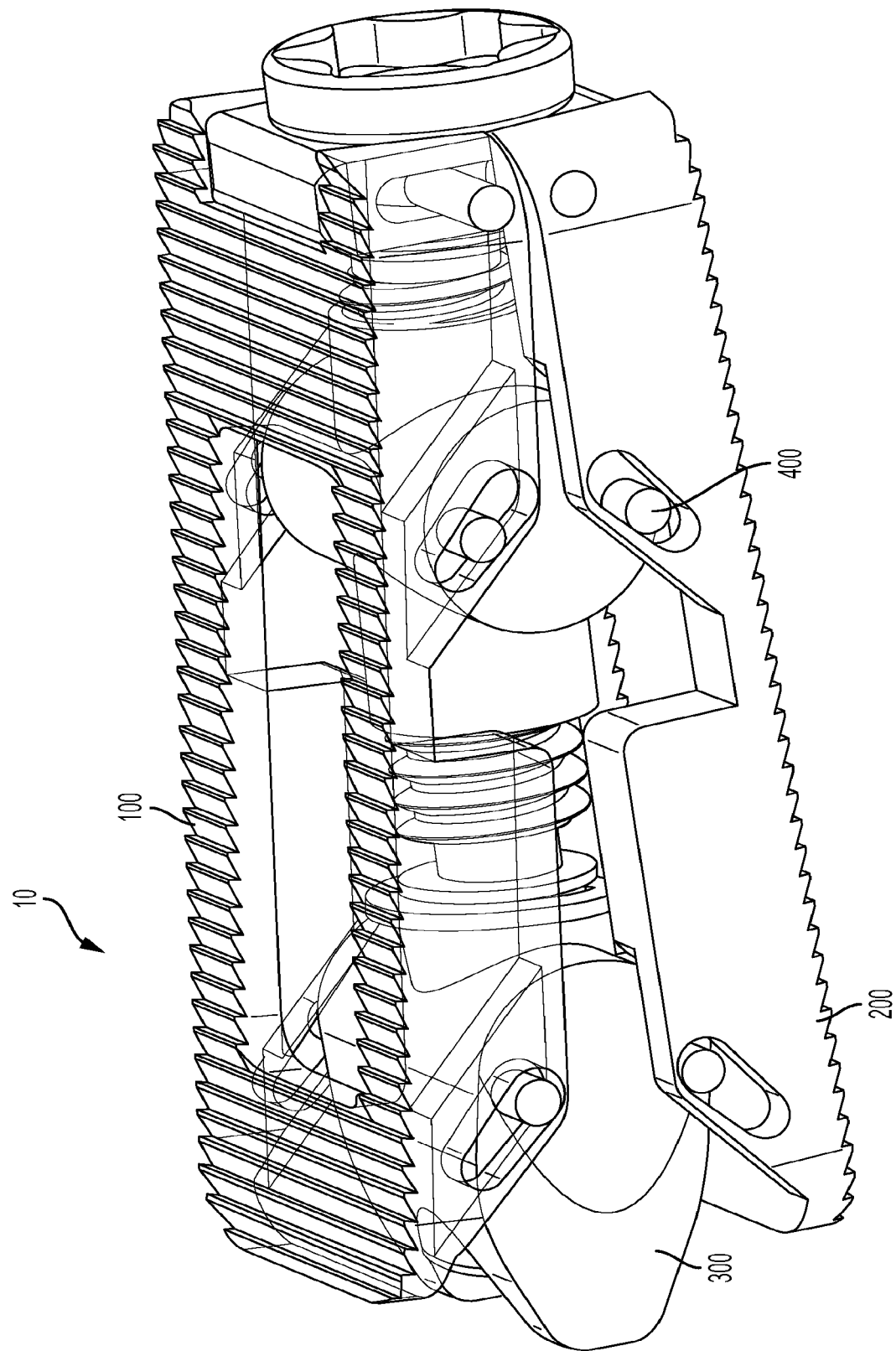
FIG. 18 is a perspective view of the inter-body fusion device of FIG. 13 in the second expanded position, in which the device angle between the first plate and the second plate is greater than 0 degrees and in which the first plate is illustrated transparently for clarity.

In one aspect, the distal end 404 of at least one pin 400 can be coupled to the longitudinal sidewall 314 of the first member 302, and the distal end of at least one pin can be coupled to the longitudinal sidewall 330 of the second member so that the proximal end 402 of each pin can extend into a respective slot (such as the third slot 150 and the fourth slot 152 of the first plate 100, and the fifth slot 250 and the sixth slot 252 of the second plate 200). Thus, when assembled, a portion of each pin can slide in a slot and allow the first plate, the second plate, and/or the insert 300 to move relative to each other When assembled, the device is adjustable about and between a first unexpanded position and a second expanded position. In the first unexpanded position, as illustrated in FIG. 13, a portion of the inner surface 120 of the first plate 100 and the inner surface 220 of the second plate 200 can contact each other and/or, a portion of a pin can contact the leading end 154, 254 of each respective slot 148, 248. In the first unexpanded position, each of the first member 302 and the second member 304 of the insert 300 can be positioned substantially within the interior cavity 15 formed between the substantially aligned longitudinal sidewalls 130, 230 of the first and second plates 100, 200. In the second expanded position, as illustrated in FIG. 15, a portion of the inner surface 120 of the first plate 100 and the inner surface 220 of the second plate 200 can be spaced from each other a predetermined distance and/or, a portion of a pin can contact the trailing end 156, 256 of each respective slot 148, 248. In the second expanded position, each of the first member 302 and the second member 304 of the insert 300 can be positioned substantially within the interior cavity 15 formed between the substantially aligned longitudinal sidewalls 130, 230 of the first and second plates 100, 200. As can be appreciated, in the second expanded position, the inter-body fusion device 10 can have a height and interior cavity 15 volume that is greater than the height and interior cavity volume of the inter-body fusion device in the first, unexpanded position. Thus, in the first unexpanded position, the interior cavity 15 of the device can have a first cavity size, and in the second expanded position the interior cavity has a second cavity size that is greater than the first cavity size.

In one aspect, in the first, unexpanded position, the longitudinal axis $L_1$ of the first plate 100 and the longitudinal axis $L_2$ of the second plate 200 can be substantially parallel to each other or, optionally, the longitudinal axis $L_1$ of the first plate and the longitudinal axis $L_2$ of the second plate can be at an acute angle relative to each other. In another aspect, in the second, expanded position, the longitudinal axis $L_1$ of the first plate 100 and the longitudinal axis $L_2$ of the second plate 200 can be substantially parallel to each other or, optionally, the longitudinal axis $L_1$ of the first plate and the longitudinal axis $L_2$ of the second plate can be at an acute angle relative to each other.

In order to selectively expand the inter-body fusion device 10 of FIGS. 13-20 about and between the first unexpanded position and the second expanded position, at least the one of first member 302 or the second member 304 of the insert 300 can be moved longitudinally about and between a first insert position and a second insert position. In one aspect, in the first insert position, the trailing edge 308 of the first member can be spaced from the trailing edge 104 of the first plate 100 an unexpanded first distance and the trailing edge 324 of the second member can be spaced from the trailing edge 104 of the first plate 100 an unexpanded second distance. In another aspect, in the second insert position, the trailing edge 308 of the first member can be spaced from the trailing edge 104 of the first plate 100 an expanded first distance that is less than the unexpanded first distance, and the trailing edge 324 of the second member can be spaced from the trailing edge 104 of the first plate an expanded second distance that is less than the unexpanded second distance.

When adjusting the inter-body fusion device 10 of this embodiment about and between the first unexpanded position and the second expanded position, the first member 302 and the second member 304 of the insert 300 do not necessarily need be moved simultaneously or to the same insert position. For example, the first member can be in the first insert position while the second member can be in the second insert position. In another example, the first member 302 can be in the second insert position while the second member 304 can be in the first insert position. Thus, the first member and the second member can be in any insert position between the first insert position and the second insert position at any time regardless of the position of the other member.

Upon moving the first member 302 towards the second insert position, at least a portion of the at least one pin 400 coupled to or formed integrally with the first member can be moved into contact with a wall of the third slot 150 in the first plate 100 and/or the fifth slot 250 in the second plate. The pin can slide therein the slot from the leading end 154, 254 of the slot towards the trailing end 156, 256 of the respective slot. If the slot is at an angle relative to the longitudinal axis $L_1$ of the first plate 100, then, the inclined wall of the slot can urge the first plate and/or the second plate 200 away from each other. For example, if the slot angle is an acute angle or a right angle, the pin sliding in the slot can urge the first plate 100 and/or the second plate 200 away from each other in the direction of the slot.

Similarly, upon moving the second member 304 towards the second insert position, at least a portion of the at least one pin 400 coupled to or formed integrally with the second member can be moved into contact with a wall of the fourth slot 152 of the first plate 100 and/or the sixth slot 252 of the second plate. The pin can slide therein the slot from the leading end 154, 254 of the slot towards the trailing end 156, 256. If the respective slot is at an angle relative to the longitudinal axis $L_1$ of the first plate 100, then, the inclined wall of the slot can urge the first plate and/or the second plate 200 away from each other.

In use, the second member driver 504 can be coupled to the distal end 337 of the second member 304. If the device is in the first, unexpanded position, rotation of the handle 506 can cause the first member 302 and the second member 304 of the insert to move from the first insert position towards the second insert position (that is, rotation of the handle can cause the first member and the second member a to move longitudinally toward the trailing edge 104 of the first plate 100), thereby urging the first plate and second plate away from each other. Upon reaching the desired device height, the second member driver can be removed from the second member 304, and a separate first member driver 502 can be inserted through the longitudinal duct 339 of the second threaded shaft 336 of the second member and through the longitudinal pathway 334 of the second member so that the first member driver can be coupled to the distal end 319 of the first threaded shaft 318 of the first member 302. Rotation of the first member driver can cause the first member to move longitudinally, thereby changing the angle between the first plate and the second plate (the device angle). For example, rotation of the first member driver in a first direction can cause the first member 302 to move longitudinally towards the trailing edge 104 of the first plate, thereby increasing the device angle. In another example, rotation of the first member driver 502 in a second direction that is opposed to the first direction can cause the first member 302 to move longitudinally towards the leading edge 102 of the first plate 100, thereby decreasing the device angle. When the desired device angle has been reached, the first member driver can be removed from the device 10.

A third embodiment of the inter-body fusion device 10 is illustrated in FIGS. 21-28, according to one aspect. In this embodiment, the inter-body fusion device can be as described above, comprising a first plate 100, a second plate 200, and an insert 300. Optionally, however, the insert can be a coupled to a portion of the second plate.

The second plate 200 of this embodiment comprise a mounting surface 258 and at least one sleeve 260 having an internal sleeve diameter fixedly attached thereto. Each sleeve can be configured to couple a portion of the insert to the second plate. For example, a first sleeve 262 can be attached to the mounting surface so that a portion on the second member 304 of the insert can slide through the first sleeve. That is, the first sleeve can act as a bushing to maintain the longitudinal axis $L_3$ of the insert in substantial alignment with the longitudinal axis $L_2$ of the second plate as the second member 304 of the insert moves longitudinally relative to the second plate 200. In another aspect, a second sleeve 264 can be positioned near or adjacent to the trailing edge 204 of the second plate and can act similar to the second retainer 238 to couple a portion of the second member 304 to the second plate 200. At least one pin bore 266 can be defined therein a portion of a longitudinal sidewall 268 of the first and/or second sleeve. In a further aspect, a longitudinal groove 272 can be defined in the mounting surface 258, the longitudinal groove sized and shaped so that a portion of an outer surface 301 of the first member 302 and/or the second member 304 can slide therein. The shoulder 346 of the second threaded shaft can engage a portion of the second sleeve 264 and/or the second plate 200 to restrict movement of the second threaded shaft longitudinally towards the leading edge 202 of the second plate.

Rotation of the second threaded shaft 336 can cause the distance between the trailing edge 324 of the second member 304 and the second sleeve 264 to change. For example, rotation of the second threaded shaft in a first direction can make the distance between the trailing edge of the second member and the second sleeve smaller. In another example, rotation of the second threaded shaft 336 in a second direction that is opposed to the first direction can make the distance between the trailing edge 324 of the second member 304 and the second sleeve 264 larger.

The at least one pin 400 can comprise a plurality of pins. In one aspect, at least one pin of the plurality of pins can be coupled to or formed integrally with the first member 302 and/or the second member 304 of the insert. In another aspect, the distal end 404 of the at least one pin can be securely attached to or formed integrally with the outer surface 301 of the first member and/or the second member. In another aspect, at least one pin can be positioned on the first member 302 and/or the second member 304 such that a longitudinal axis of the pin $L_4$ is substantially transverse to the longitudinal axis $L_3$ of the insert 300. The proximal end 402 of the pin can extend away from the outer surface and can be configured to engage at least one slot 148 defined in the first plate 100.

Figure 21:
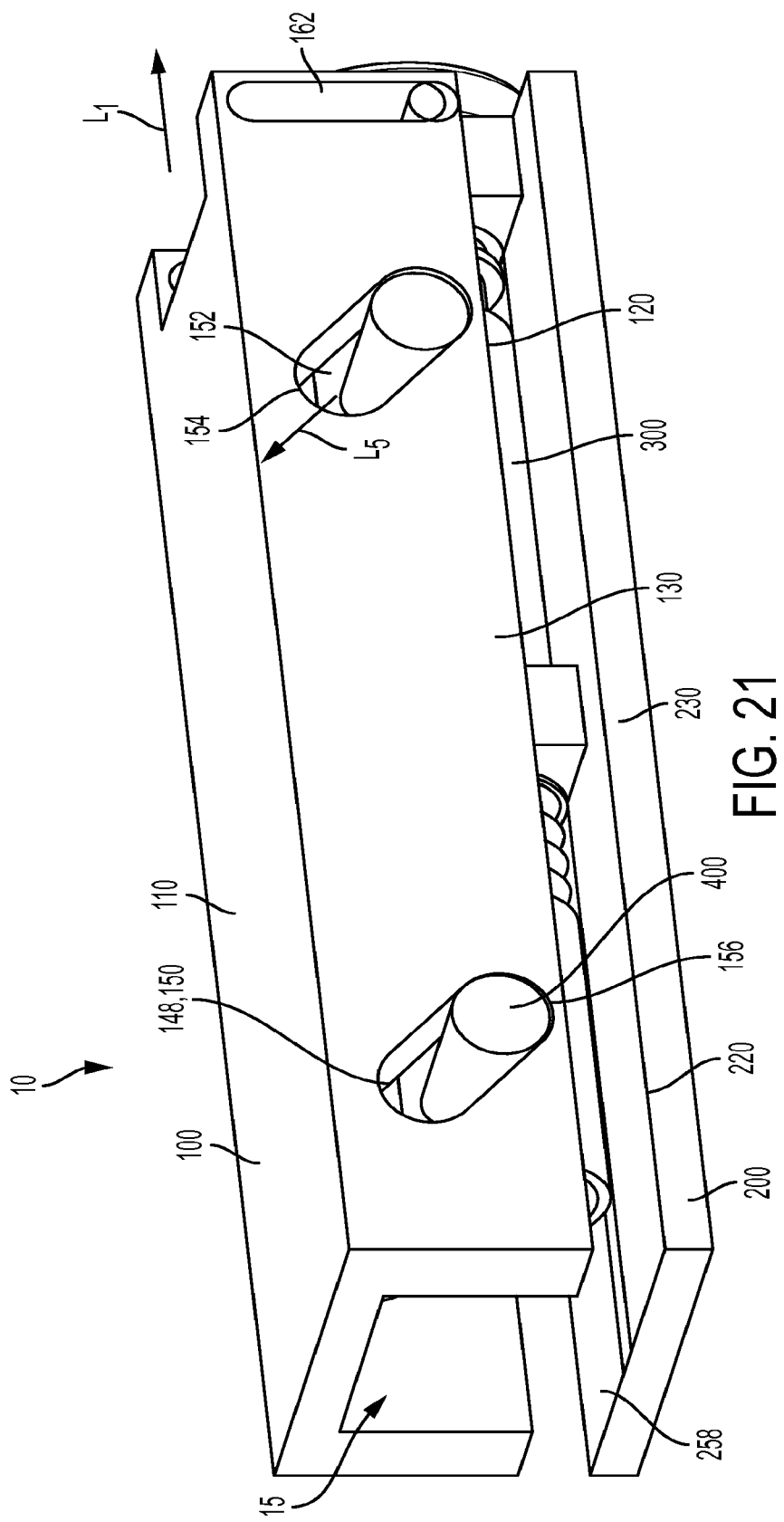
FIG. 21 is a front perspective view of a third embodiment of an expandable, adjustable inter-body fusion device in a second expanded position, the device comprising a first plate, a second plate and an insert, and in which a device angle between the first plate and the second plate is substantially 0 degrees, according to one aspect.
Figure 22:
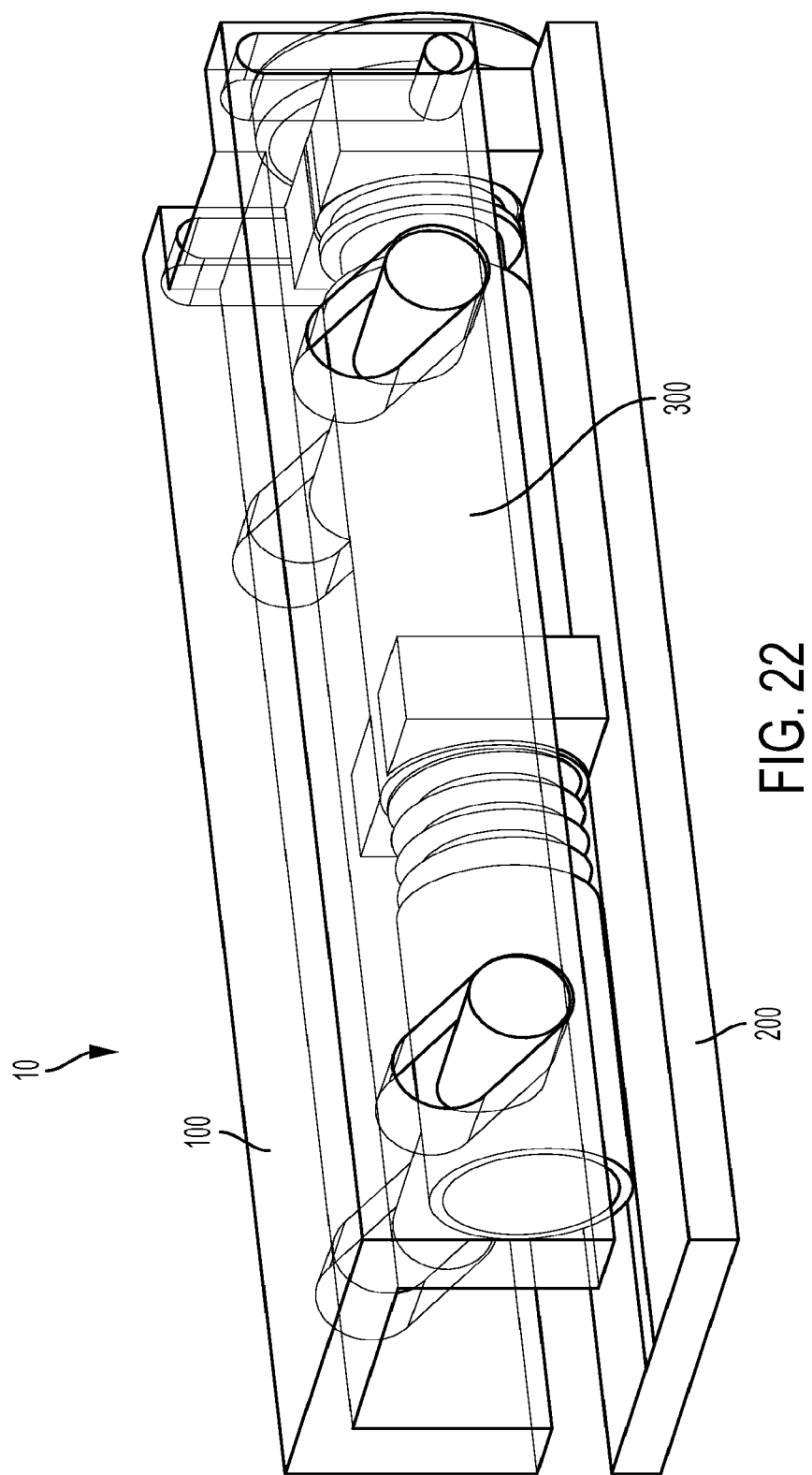
FIG. 22 is a perspective view of the inter-body fusion device of FIG. 21 in the second expanded position, in which the first plate is illustrated transparently for clarity.

With reference now to FIG. 21, the at least one slot 148 can be defined in the longitudinal sidewall 130 of the first plate 100, and the at least one slot of the first plate can comprise the third slot 150 and the fourth slot 152. In one aspect, a seventh slot 162 can be defined in the longitudinal sidewall of the first plate near or adjacent to the trailing edge 104 of the first plate 100. Each slot of the at least one slot can have the leading end 154 and the trailing end 156, with the leading end being positioned closed to the upper bone contact surface 110 of the first plate than the trailing end. In another aspect, the third slot, the fourth slot and/or the seventh slot can be positioned along the slot axis $L_5$ that is substantially transverse to the longitudinal axis $L_1$ of the first plate 100. Optionally, however, the slot axis $L_5$ of the third slot 150, the fourth slot 152 and/or the seventh slot 162 can be at an acute slot angle relative to the longitudinal axis $L_1$ of the first plate. In another aspect, the third slot, the fourth slot and/or the seventh slot can be substantially parallel to each other. The third slot 150 can be sized, shaped and positioned to engage the proximal end 402 of a pin 400 coupled to the first member 302, and the fourth slot can be sized, shaped and positioned to engage the proximal end of a pin coupled to the second member 304. The seventh slot 162 can be sized, shaped and positioned to engage the proximal end 402 of a pin 400 coupled to the second sleeve 264.

To assemble the inter-body fusion device 10 according to this embodiment, the insert 300 can be coupled to the second plate 200. For example, the leading edge 322 of the second member 304 can be inserted through the first sleeve 262, and the first threaded shaft 318 of the first member 302 can complementarily engage a portion of the threads of the second bore 332 of the second member 304. A portion of the second threaded shaft 336 can be inserted through the second sleeve 264 and the second threaded shaft can complementarily engage a portion of the threads of the second bore 332.

The distal end 404 of at least one pin 400 can be coupled to the pin bore 266 of the second sleeve 264 so that the proximal end 402 of each pin can extend into the seventh slot 162 of the first plate. Thus, when assembled, a portion of the pin can slide in the seventh slot and allow the first plate 100 and the second plate 200 to move relative to each other. In one aspect, the distal end 404 of at least one pin 400 can be coupled to the outer surface 301 of the first member 302 and/or the distal end of at least one pin can be coupled to the outer surface of the second member 304 so that the proximal end 402 of each pin can extend into a slot, such as the third slot 150 and the fourth slot 152 of the first plate 100. Thus, when assembled, a portion of each pin can slide in a slot and allow the first plate to move relative to the second plate.

Figure 23:
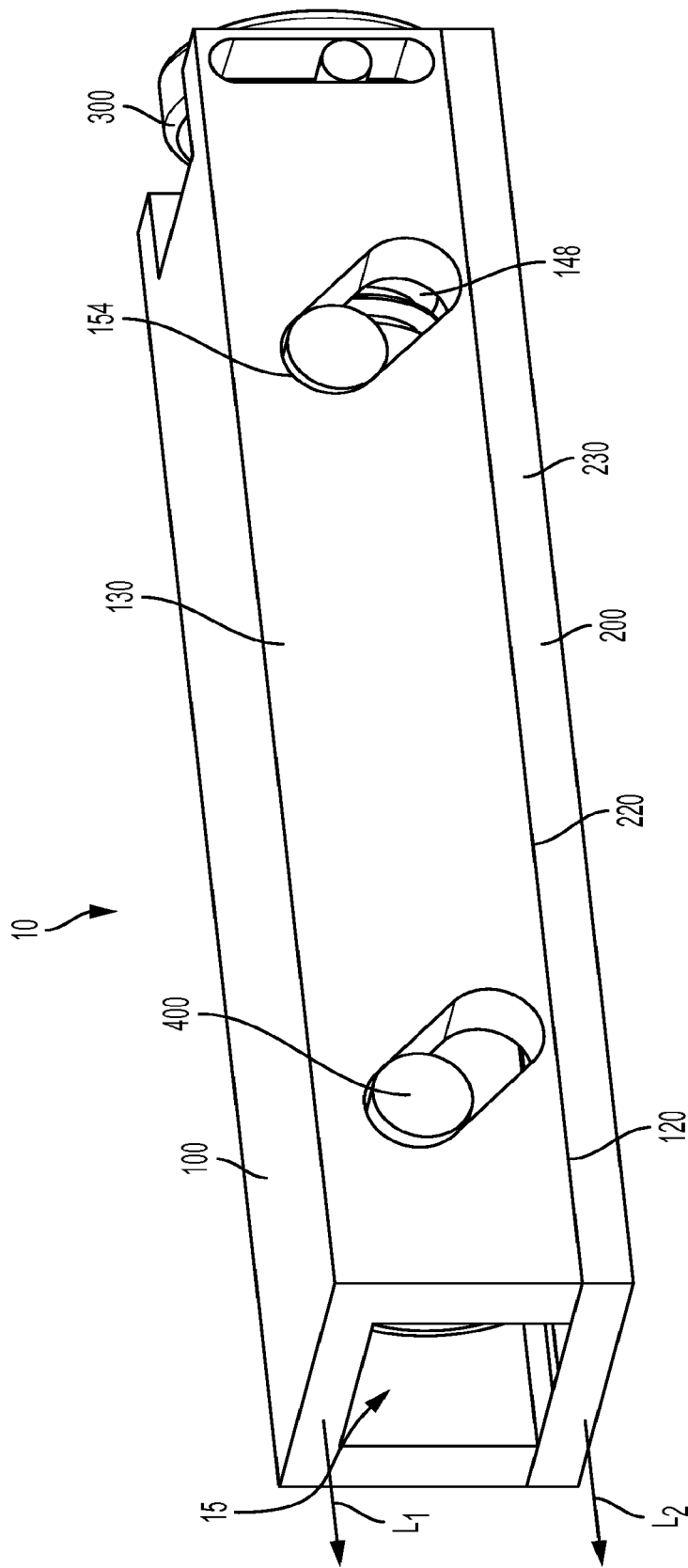
FIG. 23 is a perspective view of the inter-body fusion device of FIG. 21 in a first unexpanded position.
Figure 24:
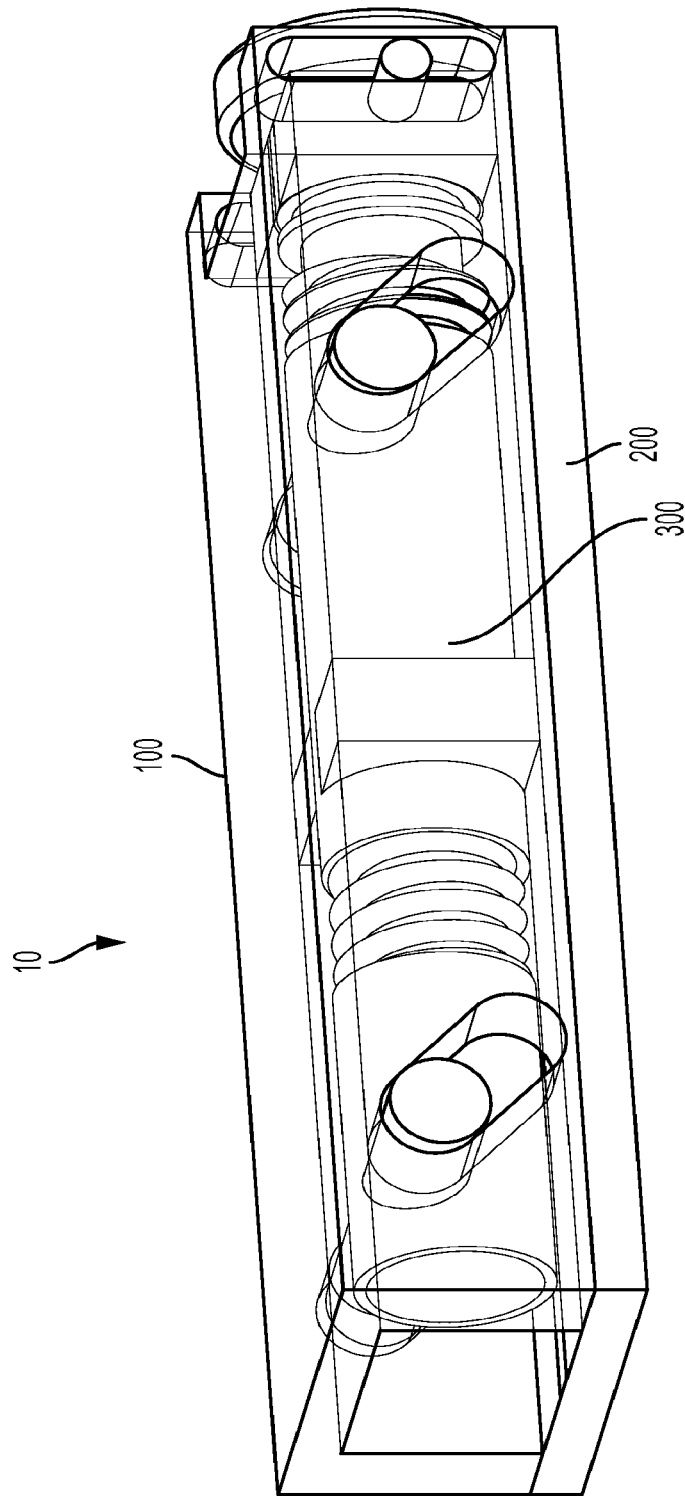
FIG. 24 is a perspective view of the inter-body fusion device of FIG. 21 in the first unexpanded position, in which the first plate is illustrated transparently for clarity.
Figure 25:
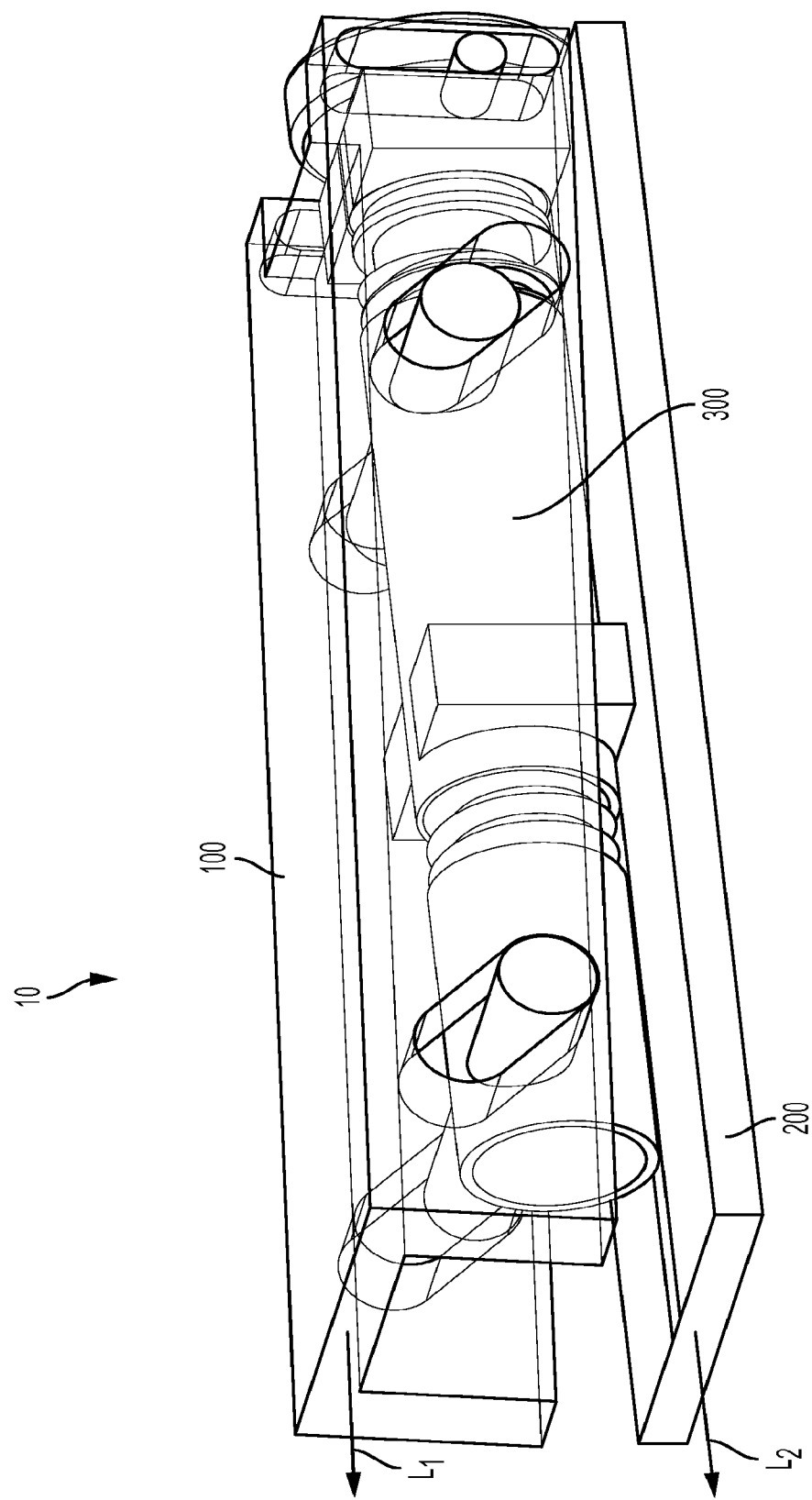
FIG. 25 is a perspective view of the inter-body fusion device of FIG. 21 in the second expanded position, in which the device angle between the first plate and the second plate is greater than 0 degrees and in which the first plate is illustrated transparently for clarity.

When assembled, the inter-body fusion device 10 is adjustable about and between a first unexpanded position and a second expanded position. In the first unexpanded position, as illustrated in FIG. 23, a portion of the inner surface 120 of the first plate 100 and the inner surface 220 of the second plate 200 can contact each other and/or, a portion of a pin 400 can contact the leading end 154 of a slot 148. In the first unexpanded position, each of the first member 302 and the second member 304 of the insert 300 can be positioned substantially within the interior cavity 15 formed between the substantially aligned longitudinal sidewalls 130, 230 of the first and second plates 100, 200. In the second expanded position, as illustrated in FIG. 21, a portion of the inner surface 120 of the first plate 100 and the inner surface 220 of the second plate 200 can be spaced from each other a predetermined distance and/or, a portion of a pin can contact the trailing end 156 of a slot 148. In the second expanded position, each of the first member 302 and the second member 304 of the insert 300 can be positioned substantially within the interior cavity 15 formed between the substantially aligned longitudinal sidewalls 130, 230 of the first and second plates 100, 200. As can be appreciated, in the second expanded position, the inter-body fusion device 10 can have a height and interior cavity 15 volume that is greater than the height and interior cavity volume of the inter-body fusion device in the first, unexpanded position. Thus, in the first unexpanded position, the interior cavity 15 of the device can have a first cavity size, and in the second expanded position the interior cavity has a second cavity size that is greater than the first cavity size.

In one aspect, in the first, unexpanded position, the longitudinal axis $L_1$ of the first plate 100 and the longitudinal axis $L_2$ of the second plate 200 can be substantially parallel to each other or, optionally, the longitudinal axis $L_1$ of the first plate and the longitudinal axis $L_2$ of the second plate can be at an acute angle relative to each other. In another aspect, in the second, expanded position, the longitudinal axis $L_1$ of the first plate 100 and the longitudinal axis $L_2$ of the second plate 200 can be substantially parallel to each other or, optionally, the longitudinal axis $L_1$ of the first plate and the longitudinal axis $L_2$ of the second plate can be at an acute angle relative to each other.

In order to selectively expand the inter-body fusion device 10 of FIGS. 21-28 about and between the first unexpanded position and the second expanded position, at least the one of first member 302 or the second member 304 of the insert 300 can be moved longitudinally about and between a first insert position and a second insert position. In one aspect, in the first insert position, the trailing edge 308 of the first member can be spaced from the trailing edge 204 of the second plate 200 an unexpanded first distance and the trailing edge 324 of the second member can be spaced from the trailing edge 204 of the second plate an unexpanded second distance. In another aspect, in the second insert position, the trailing edge 308 of the first member can be spaced from the trailing edge 204 of the second plate 200 an expanded first distance that is less than the unexpanded first distance, and the trailing edge 324 of the second member can be spaced from the trailing edge 204 of the second plate an expanded second distance that is less than the unexpanded second distance.

When adjusting the inter-body fusion device 10 of this embodiment about and between the first unexpanded position and the second expanded position, the first member 302 and the second member 304 of the insert 300 do not necessarily need be moved simultaneously or to the same insert position. For example, the first member can be in the first insert position while the second member can be in the second insert position. In another example, the first member 302 can be in the second insert position while the second member 304 can be in the first insert position. Thus, the first member and the second member can be in any insert position between the first insert position and the second insert position at any time regardless of the position of the other member.

Upon moving the first member 302 towards the second insert position, at least a portion of the at least one pin 400 coupled to or formed integrally with the first member can be moved into contact with a wall of the third slot 150 in the first plate 100. The pin can slide therein the slot from the leading end 154 of the slot towards the trailing end 156 of the slot. If the slot is at an angle relative to the longitudinal axis $L_1$ of the first plate 100, then, the inclined wall of the slot can urge the first plate away from the second plate. For example, if the slot angle is an acute angle or a right angle, the pin sliding in the slot can urge the first plate 100 away from the second plate in the direction of the slot.

Similarly, upon moving the second member 304 towards the second insert position, at least a portion of the at least one pin 400 coupled to or formed integrally with the outer surface 301 of the second member can be moved into contact with a wall of the fourth slot 152 of the first plate 100. The pin can slide therein the slot from the leading end 154 of the slot towards the trailing end 156. If the respective slot is at an angle relative to the longitudinal axis $L_1$ of the first plate 100, then, the inclined wall of the slot can urge the first plate away from the second plate 200.

In use, the second member driver 504 can be coupled to the distal end 337 of the second member 304. If the device is in the first, unexpanded position, rotation of the handle 506 can cause the first member 302 and the second member 304 of the insert to move from the first insert position towards the second insert position (that is, rotation of the handle can cause the first member and the second member to move longitudinally toward the trailing edge 104 of the first plate 100). As the first and second members move longitudinally, the pin 400 coupled to the first member engages the third slot 150 and the pin coupled to the second member engages the fourth slot 152. The angle of the slots relative to the longitudinal axis $L_2$ of the second plate can cause the pin to urge the first plate in the slot direction thereby urging the first plate 100 away from the second plate.

Upon reaching the desired device height, the second member driver can be removed from the second member 304, and the first member driver 502 can be inserted through the longitudinal duct 339 of the second threaded shaft 336 of the second member and through the longitudinal pathway 334 of the second member so that the first member driver can be coupled to the distal end 319 of the first threaded shaft 318 of the first member. Rotation of the first member driver can cause the first member to move longitudinally so that the pin 400 coupled to the first member engages the third slot 150, and the angle of the slot relative to the longitudinal axis $L_2$ of the second plate can cause the pin to urge the first plate in the slot direction. Thus, this changes the angle between the first plate and the second plate (the device angle). For example, rotation of the first member driver in a first direction can cause the first member 302 to move longitudinally towards the trailing edge 104 of the first plate, thereby increasing the device angle. In another example, rotation of the first member driver 502 in a second direction that is opposed to the first direction can cause the first member 302 to move longitudinally towards the leading edge 102 of the first plate 100, thereby decreasing the device angle. When the desired device angle has been reached, the first member driver can be removed from the device 10.

Also presented herein are methods of using an inter-body fusion device 10 during an inter-body fusion procedure. In one aspect, the method comprises accessing the desired disc space, choosing the inter-body fusion device size with the appropriate height, inserting the inter-body fusion device 10 into the desired area in the disc space, expanding the inter-body fusion device from the first unexpanded position to the second expanded position with longitudinal movement of the insert 300, and adjusting the angle of the of the first plate 100 relative to the second plate. An additional step of packing the interior cavity 15 via the longitudinal duct 339 of the second threaded shaft 336 and the longitudinal pathway 334 of the second member 304 with bone fusion material after expansion is also contemplated. In one aspect, the method of using an inter-body fusion device 10 during an inter-body fusion procedure further comprises the step of securing the insert to the first and second plates. In another aspect, the method of using an inter-body fusion device during an inter-body fusion procedure further comprises the step of securing the inter-body fusion device 10 to the surrounding bony structure.

In one aspect, the step of choosing the inter-body fusion device 10 size with the appropriate height and angle comprises placing an undersized trial device in the disc space, expanding the trial device to the second expanded position, and repeating until the correct height and lordosis is found. The trial height and angle gives the information to prescribe the correct inter-body fusion device for the procedure.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

The invention claimed is:

1. A method of using an expandable inter-body fusion device during an interbody fusion procedure, the method comprises:
   inserting an expandable inter-body fusion device into a patient, the device comprising:
   a first plate having a longitudinal axis $L_1$ extending between a first end and a second end and an upper bone contact surface;
   a second plate having a longitudinal axis $L_2$ extending between a first end and a second end and a lower bone contact surface; the first end of the first plate disposed over and spaced a first distance from the first end of the second plate and the second end of the first plate disposed over and spaced a second distance from the second end of the second plate; and
   an insert disposed between the first plate and the second plate, wherein the insert comprises a first member and a second member along an insert longitudinal axis $L_3$ between the longitudinal axes $L_1$ and $L_2$, wherein the first member is selectively adjustable positionally such that the height of the device can be selectively adjusted and that a device angle between the upper bone contact surface and the lower bone contact surface are adjustable independently from the second member and the second member is similarly selectively positionally adjustable independently from the first member, wherein the second member includes a bore along the insert longitudinal axis $L_3$ that is configured to allow insertion of an actuation device through the bore to engage a portion of the first member;

wherein the first member is adjustable along the insert longitudinal axis $L_3$ to increase or decrease the first distance and the second member is adjustable along the insert longitudinal axis $L_3$ to increase or decrease the second distance, and expanding the expandable inter-body fusion device from an unexpanded position having a first interior cavity volume to an expanded position having a second interior cavity volume that is greater than the first interior cavity volume.

2. The method of claim 1, wherein the first plate includes at least one ramp having an inclined surface at an angle relative to the axis $L_1$.

3. The method of claim 2, wherein the first member interacts with the at least one ramp of the first plate to increase or decrease the first distance.

4. The method of claim 3, wherein the first plate includes two sidewalls and a void is defined between the two sidewalls, and wherein the void is sized and shaped to receive a portion of the second member.

5. The method of claim 1, wherein the second plate includes at least one ramp having an inclined surface at an angle relative to the axis $L_2$.

6. The method of claim 5, wherein the first member interacts with the at least one ramp of the second plate to increase or decrease the first distance.

7. The method of claim 5, wherein the first plate includes two sidewalls and a void is defined between the two sidewalls, and wherein the void is sized and shaped to receive a portion of the second member.

8. The method of claim 1, wherein, in a fully unexpanded position of the first and second ends of the first plate and the first and second ends of the second plate, the first plate is substantially parallel to the second plate.

9. The method of claim 1, wherein in a fully expanded position of the first and second ends of the first plate and the first and second ends of the second plate, the first plate is substantially parallel to the second plate.

* * * * *